US010385377B2

(12) United States Patent
Takechi et al.

(10) Patent No.: US 10,385,377 B2
(45) Date of Patent: Aug. 20, 2019

(54) BIOSENSOR AND DETECTION DEVICE

(71) Applicant: NLT TECHNOLOGIES, LTD., Kawasaki, Kanagawa (JP)

(72) Inventors: Kazushige Takechi, Kawasaki (JP); Shinnosuke Iwamatsu, Yamagata (JP); Yutaka Abe, Yamagata (JP); Toru Yahagi, Yamagata (JP); Shunsuke Konno, Yamagata (JP); Mutsuto Katoh, Yamagata (JP)

(73) Assignee: NLT TECHNOLOGIES, LTD., Kawasaki (JP)

( * ) Notice: Subject to any disclaimer, the term of this patent is extended or adjusted under 35 U.S.C. 154(b) by 313 days.

(21) Appl. No.: 15/267,683

(22) Filed: Sep. 16, 2016

(65) Prior Publication Data

US 2017/0082570 A1    Mar. 23, 2017

(30) Foreign Application Priority Data

Sep. 18, 2015    (JP) .................................. 2015-185236

(51) Int. Cl.
  *C12Q 1/00*    (2006.01)
  *G01N 27/414*  (2006.01)
(52) U.S. Cl.
  CPC ............. *C12Q 1/006* (2013.01); *C12Q 1/002* (2013.01); *G01N 27/4145* (2013.01); *G01N 2333/90206* (2013.01)
(58) Field of Classification Search
  CPC . G01N 27/4145; G01N 27/30; G01N 27/4075
  See application file for complete search history.

(56) References Cited

U.S. PATENT DOCUMENTS

| 4,968,400 A * | 11/1990 | Shimomura ........... C12Q 1/004 204/403.11 |
| 2009/0267057 A1 | 10/2009 | Setayesh et al. |
| 2010/0126885 A1 | 5/2010 | Iechi et al. |
| 2015/0276663 A1* | 10/2015 | Takechi ............... G01N 27/414 257/253 |

FOREIGN PATENT DOCUMENTS

| EP | 0235024 B1 * | 11/1994 | ............. C12Q 1/001 |
| JP | S64-59058 A | 3/1989 | |

(Continued)

OTHER PUBLICATIONS

JP-2006010379-A, English equivalent of the abstract (Year: 2006).*

(Continued)

*Primary Examiner* — Susan D Leong
(74) *Attorney, Agent, or Firm* — Sughrue Mion, PLLC

(57) ABSTRACT

A TFT biosensor includes a gate electrode (silicon substrate), a reference electrode, and enzyme that is fixed to an insulating substrate spatially separated from the gate electrode and the reference electrode. A pH variation in the vicinity of an ion-sensitive insulating film is induced by a reaction between the enzyme and a sensing object material. The TFT biosensor can detect a concentration of the sensing object material with high sensitivity by detecting the pH variation as a threshold voltage shift of characteristics of a gate-source voltage to a source-drain current.

9 Claims, 18 Drawing Sheets

(56) References Cited

FOREIGN PATENT DOCUMENTS

| JP | 2006010379 A | * | 1/2006 |
|----|--------------|---|--------|
| JP | 2009-539241 A | | 11/2009 |
| JP | 2010-151540 A | | 7/2010 |
| JP | 2011-185818 A | | 9/2011 |
| JP | 2012-73101 A | | 4/2012 |
| JP | 2013-148456 A | | 8/2013 |

OTHER PUBLICATIONS

D. Gonçalves, et al., "Label-free electronic detection of biomolecules using a-Si:H field-effect devices", Journal of Non-Crystalline Solids, Jun. 15, 2006, pp. 2007-2010, vol. 352.

Wei Xue, et al., "A thin-film transistor based acetylcholine sensor using self-assembled carbon nanotubes and $SiO_2$ nanoparticles", Sensors and Actuators B: Chemical, Sep. 25, 2008, pp. 981-987, vol. 134.

A. Poghossian, et al., "An ISFET-based penicillin sensor with high sensitivity, low detection limit and long lifetime", Sensors and Actuators B: Chemical, Jun. 1, 2001, pp. 519-526, vol. 76.

Communication dated Apr. 28, 2019 issued by the China National Intellectual Property Administration in counterpart application No. 201610829596.5.

Notice of Reasons for Refusal dated May 7, 2019 issued by the Japanese Patent Office in counterpart application No. 2015-185236.

\* cited by examiner

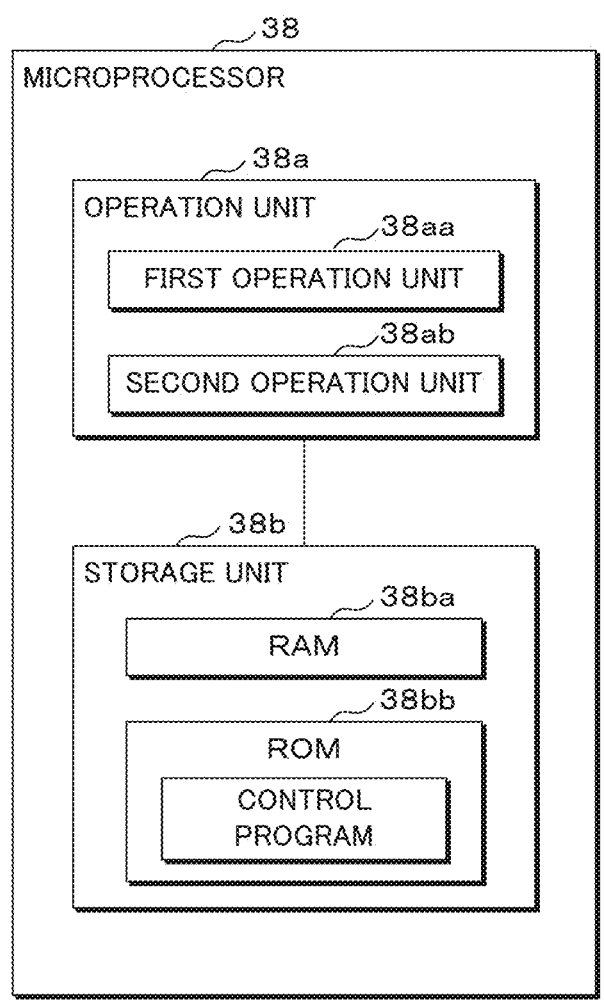

F I G. 1 6
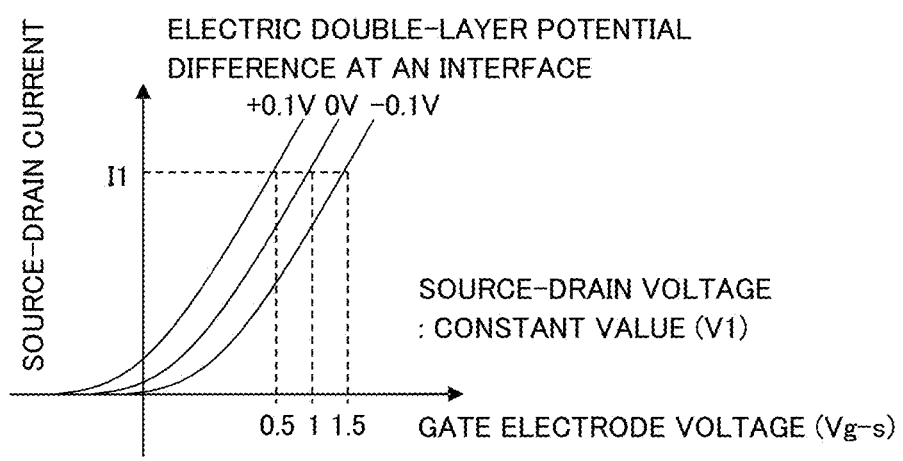

F I G. 1 7

| HYDROGEN ION CONCENTRATION [pH] | GATE ELECTRODE VOLTAGE Vg-s [V] | SOURCE-DRAIN CURRENT I1 [nA] |
| --- | --- | --- |
| 6.0 | 0.50 | 200 |
| 6.1 | 0.61 | 200 |
| 6.2 | 0.70 | 200 |
| 6.3 | 0.79 | 200 |
| 6.4 | 0.89 | 200 |
| 6.5 | 1.00 | 200 |
| 6.6 | 1.09 | 200 |
| 6.7 | 1.21 | 200 |
| 6.8 | 1.29 | 200 |
| 6.9 | 1.41 | 200 |
| 7.0 | 1.50 | 200 |

F I G. 1 8
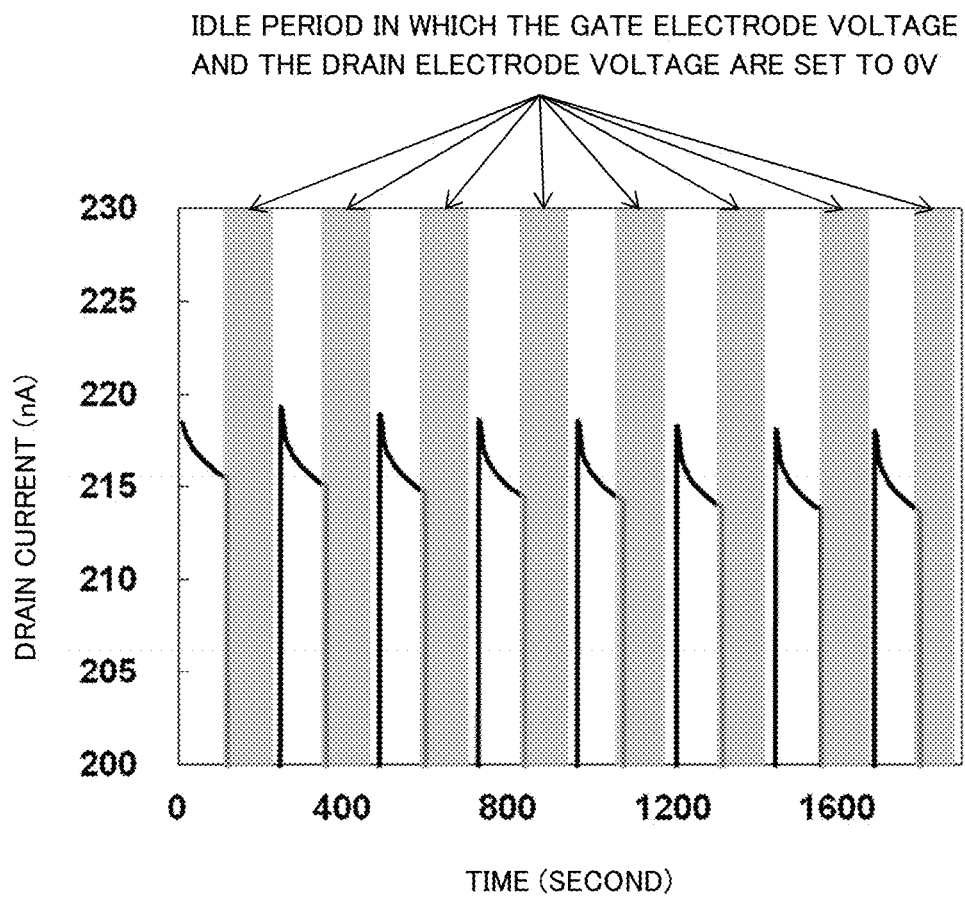

BIOSENSOR AND DETECTION DEVICE

CROSS-REFERENCE TO RELATED APPLICATIONS

This Non-provisional application claims priority under 35 U.S.C. § 119(a) on Patent Application No. 2015-185236 filed in Japan on Sep. 18, 2015, the entire contents of which are hereby incorporated by reference.

FIELD

The disclosure relates to a biosensor, and a detection device that uses the biosensor.

BACKGROUND

Recently, the biosensor, which uses a biological material recognition mechanism of biopolymer, has been used in medical and environmental analysis fields. The biosensor is obtained by combining the biological material recognition mechanism of biopolymer, an interfacial potential detection mechanism at an interface (also referred to as a solid-liquid interface) of a solution and an insulating film, and an electrical measurement device.

As the biological material recognition mechanism, substrate-specificity of enzyme, antibody-antigen reaction, a mutual operation between deoxyribonucleic acid (DNA) and DNA, a mutual operation between ribonucleic acid (RNA) and RNA, coupling of lectin and physiological active sugar chain, affinity of protein to specific biological material, and the like have been used.

As the interfacial potential detection mechanism, for example, an ion sensitive FET (FET sensor), in which a metal oxide semiconductor field effect transistor (MOSFET) is set as basic structure, has been used. The FET sensor measures an electric double-layer potential by detecting potential variation of electric double-layer that is formed at the solid-liquid interface as threshold voltage (Vth) shift of reference electrode potential-drain current characteristics (Vref-Id characteristics).

Examples of a main factor of causing the electric double-layer potential to vary include a phenomenon such as variation in potential of hydrogen (pH) in the solution, physical and chemical adsorption to the insulating film interface. For example, the relationship between the pH and the electric double-layer potential is known by electrochemical Nernst theory. For example, at 25° C., pH varies by 1 (this means that one order of magnitude of the hydrogen ion concentration in the solution is changed). The electric double-layer potential varies by approximately 59 mV due to the variation. This represents that 59 mV/pH is theoretical limit of sensor sensitivity in the pH sensor based on the electric double-layer potential.

The level of pH is useful index for bio-sensing. The biosensor causes the pH variation in the solution by decomposing the biological material through enzyme reaction, and by generating hydrogen ions as a by-product. In addition, the biosensor measures a concentration of the biological material by detecting the pH variation with the FET sensor. The biosensor has both molecular recognition and substrate decomposition function with enzyme, and pH measurement function with the FET sensor. Therefore, it is necessary for the molecular recognition and substrate decomposition function and the pH measurement function not to inhibit each other. In addition, a variation in the concentration of hydrogen ions that are generated through the enzyme reaction becomes lower than a concentration of original biological material. Therefore, so as to realize bio-sensing in which the pH variation is set as index, it is necessary to have a function capable of accurately detecting an extremely minute pH variation.

In the future, in clinical examination field, it is predicted that a demand for point of care testing (POCT), in which test is performed in the vicinity of test subject in medical field, will increase. This clinical examination is performed to grasp the concentration of specific biological material. In addition, in this clinical examination, it is considered that a demand for measurement of low-concentration material, which is not detected in an existing technology, will increase. To cope with this demand, the biosensor capable of performing high-sensitivity measurement is necessary.

Next, the descriptions will be given of technology (hereinafter, referred to as "related technology") that relates to the disclosure.

With regard to the TFT biosensor, for example, there is reported case related to label-free detection of the DNA molecules and horseradish peroxidase molecules by using an amorphous silicon TFT (D. Goncalves, and three other persons, "Label-free electronic detection of biomolecules using a-Si:H field-effect devices", "Journal of Non-Crystalline Solids", ELSEVIER, Jun. 15, 2006, volume 352, p. 2007-2010). Furthermore, the TFT is an abbreviation of a thin film transistor. A linear Vth shift is obtained up to 0.4 μM in the DNA molecules, and up to 0.1 μM in the horseradish peroxidase molecules.

In the TFT biosensor in which a carbon nanotube is used in an active layer, there is disclosed an acetylcholine sensor in which acetylcholinesterase is fixed to an upper portion of the active layer (Wei Xue, and other one person, "A thin-film transistor based acetylcholine sensor using self-assembled carbon nanotubes and $SiO_2$ nanoparticles", "Sensors and Actuators B: Chemical", ELSEVIER, Sep. 25, 2008, volume 134, p. 981-987). As sensitivity, resolution, and response time, values of 378.2 μA/decade, 10 nM, and 15 seconds are obtained, respectively.

As known example in which the enzyme reaction is used, there is reported the penicillin sensor in which penicillin oxidase is fixed to an ion-sensitive film of FET sensor (A. Poghossian, and other four persons, "An ISFET-based penicillin sensor with high sensitivity, low detection limit and long lifetime", "Sensors and Actuators B: Chemical", ELSEVIER, Jun. 1, 2001, volume 76, p. 519-526). The penicillin sensor has the configuration in which pH is allowed to vary by decomposing penicillin with the enzyme, and by generating hydrogen ions as by-product, and the pH variation is detected by FET sensor. As detection sensitivity, 120±10 mV/mM is obtained, and a continuous operation of one year or longer is confirmed.

In addition, as biosensor including a field effect transistor, the following case is reported. Specifically, a reaction field, to which a detection object material recognition molecule is fixed on one surface of a silicon substrate, and a field effect element which is formed on the other surface of the silicon substrate as a detection unit, are provided so as to attain an improvement in detection sensitivity (Japanese Patent Application Laid-Open No. 2013-148456).

In addition, there is disclosed an example of biosensor in which a vertical transistor is used as transducer, and the enzyme and antibody, which have a molecule recognition function, are fixed to porous alumina, and which indicates a possibility of high-speed response operation (Japanese Patent Application Laid-Open No. 2010-151540).

SUMMARY

As described above, examples of the biosensor are disclosed. However, all of the above-described documents have the configuration in which a gate voltage is applied by a reference electrode that is immersed in the solution containing a measurement object material, and the concentration of the measurement object material is measured from the Vth shift in Vref-Id characteristics. In this sensor, it is difficult to obtain sensitivity that is higher than theoretical sensitivity that is based on Nernst theory. As a result, it is difficult to apply the above-described configuration to measurement of the biological material having an extremely low concentration.

The pH sensor using the basic structure of MOSFET is already in practical use. When it is the try to applicate the measurement for the biological materials, it is obvious that the higher sensitivity of pH sensor is needed. It is considered that the sensitivity is equal to or lower than 59 mV/pH based on the Nernst theory is sufficient in the case of the pH measurement for the liquid solution.

When application is attempted to measurement of biological material, it is apparent that a high-sensitivity pH sensor is necessary. For example, a biological material, which becomes a measurement object of the biosensor, exists in the solution having approximately pH 7 in the concentration of approximately $10^{-7}$ to $10^{-9}$ mol/L. When the biological material is decomposed with the enzyme, and a variation, which occurs as a result of the decomposition, in the concentration of hydrogen ions is detected, it is necessary to detect a pH variation approximately in the range from 0.001 to 0.01. At this time, in the pH sensor of the related art, it is necessary to detect a minute voltage variation of 0.059 mV to 0.59 mV. In biosensors of related technologies, it is difficult to realize high-reliability measurement when considering an effect such as sensor drift, thermal fluctuation, a variation in a liquid temperature, and the like.

In addition, since the biopolymer is fixed onto the insulating film, the disclosed technologies have the structure in which a material recognition unit with the biopolymer and a pH sensing portion with the FET sensor exist in the same portion. When the biopolymer film is made thick, the pH sensing portion does not come into contact with the solution, and thus there is a concern that this situation leads to a decrease in pH sensitivity. Furthermore, a region in which the enzyme can be fixed is limited, and thus it is difficult to increase the amount of pH variation due to the enzyme reaction. That is, this leads to a problem in which it is difficult to raise detection sensitivity for the biological material.

In the structure of the disclosed technologies in which the enzyme is fixed onto the insulating film, basically, exchange of enzyme is difficult. Typically, it is known that in the biopolymer such as enzyme, a function thereof deteriorate with the passage of time. Therefore, the function of the biopolymer is lost in a very short period of time in comparison to an inorganic structure body. Accordingly, in the structure of the disclosed technologies in which the exchange of enzyme is difficult, when the enzyme is inactivated, even when the TFT sensor unit normally operates, a function as the biosensor is lost. This leads to a problem in which the lifetime of sensor is shortened, and a burden on a user increases.

In addition, in the configuration of the disclosed technologies, the enzyme molecule is disposed at a position that is most close to the reference electrode, and thus there is also a problem in that a decrease in activity may be caused due to application of gate voltage.

A biosensor according to an aspect of embodiments includes: a semiconductor active layer; a gate insulating film that is provided on a first surface of the semiconductor active layer, and insulates the semiconductor active layer and the gate electrode from each other; an ion-sensitive insulating film that is provided on a second surface of the semiconductor active layer, and includes a region that comes into contact with a solution; and enzyme that is fixed at a position spatially separated from the region, and reacts with a material in the solution to allow potential variation in the region to occur. Further, in the biosensor according to an aspect of embodiments, an electrostatic capacity per unit area of the ion-sensitive insulating film is greater than an electrostatic capacity per unit area of the gate insulating film.

It is to be understood that both the foregoing general description and the following detailed description are exemplary and explanatory and are not restrictive of the invention.

BRIEF DESCRIPTION OF THE DRAWINGS

FIG. 15 is a view illustrating a configuration example of a microprocessor of a TFT biosensor device;

FIG. 16 is an explanatory view illustrating a measurement principle in the TFT biosensor device of the eighth embodiment;

FIG. 17 is a view illustrating a table in which correspondence between a concentration of hydrogen ions and a gate electrode voltage is stored; and FIG. 18 is an explanatory view of a measurement method in a TFT biosensor device in Example 12.

DETAILED DESCRIPTION

Figure 1:
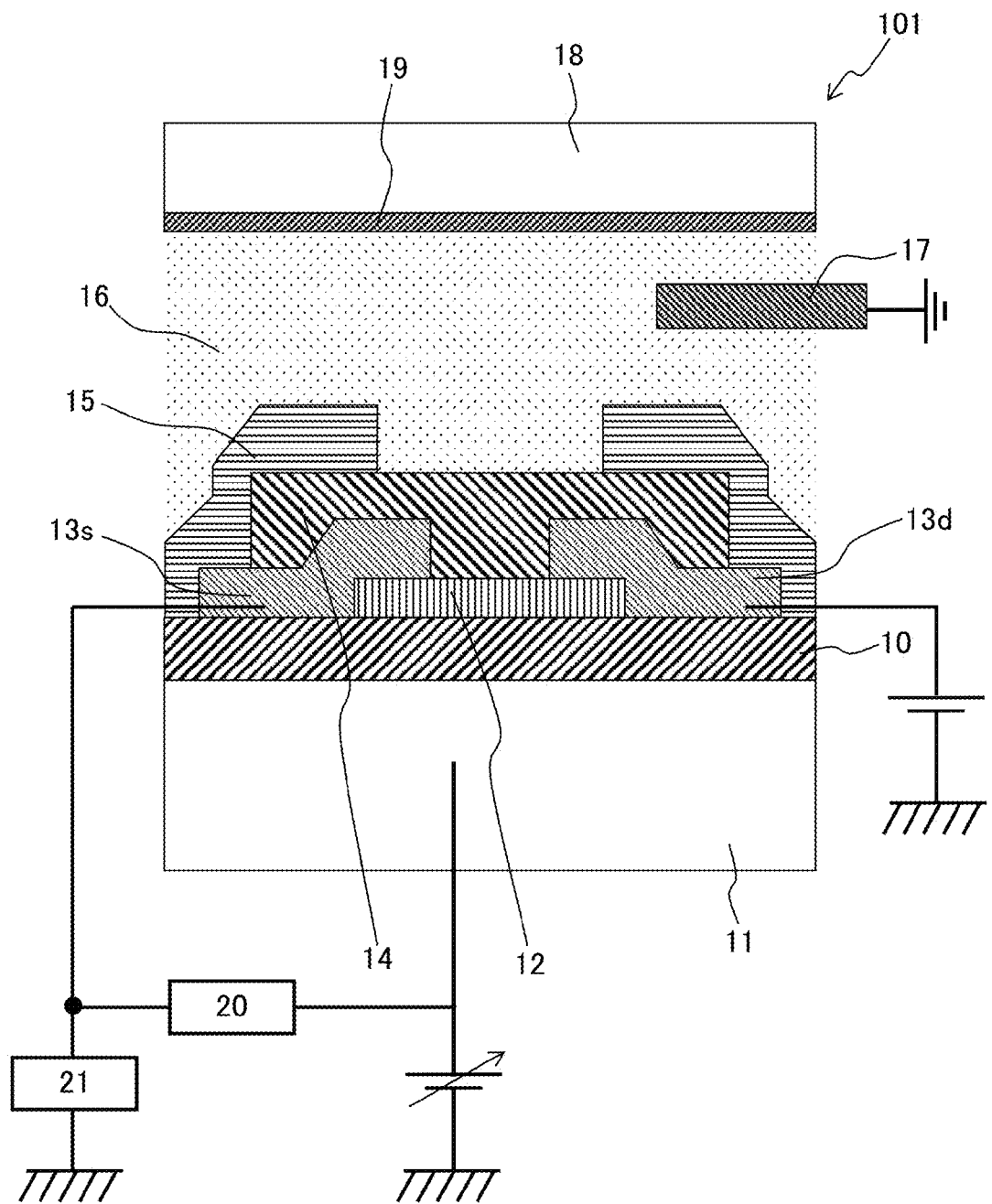
FIG. 1 is a cross-sectional view illustrating a TFT biosensor of first embodiment.

Hereinafter, embodiments for carrying out the disclosure (hereinafter, referred to as "embodiments") will be described with reference to the accompanying drawings. Furthermore, in this specification and the drawings, the same reference numeral will be given to substantially the same constituent element. A shape in the drawings is illustrated for easy comprehension of those skilled in the art, and does not entirely match actual dimensions and ratios.

In the following embodiments, the descriptions will be given of biosensor that is constituted by using TFT, and thus the biosensor will be referred to as the TFT biosensor.

(First Embodiment)

FIG. 1 is the cross-sectional view illustrating a TFT biosensor 101 of first embodiment.

The TFT biosensor 101 includes a semiconductor active layer 12 to which a source electrode 13s and a drain electrode 13d are connected. A thermal oxide film 10 as a gate insulating film, and a silicon substrate 11 as a gate electrode are provided on one surface (a first surface, a lower surface in FIG. 1) of the semiconductor active layer 12. In addition, an ion-sensitive insulating film 14 and a protective insulating film 15 are provided on the other surface (a second surface, an upper surface in FIG. 1) of the semiconductor active layer 12. In addition, the TFT biosensor 101 includes a reference electrode 17 at a position that is spatially separated from the ion-sensitive insulating film 14 and the protective insulating film 15.

Furthermore, an electrostatic capacity per unit area of the ion-sensitive insulating film 14 is set to be greater than an electrostatic capacity per unit area of the gate insulating film (the thermal oxide film 10). In addition, the TFT biosensor 101 includes a second insulating substrate 18, in which enzyme 19 having substrate-specificity is disposed on one surface, at a position that is spatially separated from the ion-sensitive insulating film 14 and the protective insulating film 15. At this time, with regard to a structure, it is preferable that the silicon substrate 11 on which a TFT is formed, and the second insulating substrate 18 (enzyme 19) face each other as illustrated in FIG. 1, but may be two-dimensionally disposed such as same plane.

A space between the silicon substrate 11 and the second insulating substrate 18 is filled with a solution that includes a sensing object material 16. The protective insulating film 15 covers a region other than a region, which overlaps with a channel region of the semiconductor active layer 12, on an upper surface of the ion-sensitive insulating film 14. The ion-sensitive insulating film 14 includes a region that is not covered with the protective insulating film 15. At this region, the ion-sensitive insulating film 14 comes into contact with the solution that includes the sensing object material 16.

In addition, it is preferable that a gap between the ion-sensitive insulating film 14 and the second insulating substrate 18 is as narrow as possible so as to make diffusion of hydrogen ions generated through enzyme reaction fast, and so as to improve responsiveness of the TFT sensor. At an interface at which the ion-sensitive insulating film 14 comes into contact with the solution that includes the sensing object material 16, the ion-sensitive insulating film 14 has properties of allowing a potential in the interface to vary in response to a predetermined ion. The ion-sensitive insulating film 14 is also referred to as "ion-sensitive insulator", or "pH-sensitive transducer".

In addition, the TFT biosensor 101 further includes any one of a voltage detection unit 20 that reads out potential difference between the source electrode 13s and a gate electrode (silicon substrate 11), and a current detection unit 21 that reads out a current that flows to the source electrode 13s or the drain electrode 13d. Furthermore, in FIG. 1, both the voltage detection unit 20 and the current detection unit 21 are illustrated in the drawing.

(Example 1)

Next, Example 1, which further specifies the first embodiment, is described using FIG. 1. First, the description is given of a method of manufacturing the TFT biosensor 101 of Example 1.

An apparatus of manufacturing the TFT biosensor 101 (hereinafter, referred to as "manufacturing apparatus") forms the thermal oxide film 10 on the silicon substrate 11 in a film thickness of 200 nm. A silicon oxide film, a silicon nitride film, and the like, which are formed by plasma chemical vapor deposition (CVD) method or sputtering method, may be used instead of the thermal oxide film 10. Furthermore, the term of "manufacturing apparatus" is used as a generic name of individual apparatuses such as a film forming apparatus in sputtering or CVD, an applicator of an organic material, and an annealing oven which are necessary to manufacturing of biosensor.

In addition, the thermal oxide film 10 is formed on the silicon substrate 11, and the oxide semiconductor film composed of indium-gallium-zinc-oxygen (hereinafter, omitted as In—Ga—Zn—O) is deposited by sputtering method using metal mask. The thickness of In—Ga—Zn—O film is set at 50 nm. During the film formation, a sintered body target composed of In—Ga—Zn—O is used, the substrate is not heated, and a direct current (DC) sputtering method in mixed gas atmosphere of argon gas and oxygen gas is employed. After the film formation, the substrate is annealed in the air at 400° C. for one hour. The semiconductor active layer 12 having an island shape is formed by patterning the oxide semiconductor film.

Continuously, the source electrode 13s and the drain electrode 13d are formed by DC-sputtering of molybdenum (Mo) using the metal mask. The film thickness of the source electrode 13s and the drain electrode 13d is set at 50 nm. In addition, the ion-sensitive insulating film 14, that is, tantalum (Ta) oxide film having film thickness of 200 nm, is sputtered and patterned by using metal mask. In the film formation, a sintered body target composed of Ta—O is used, the substrate is not heated, and radio frequency (RF) sputtering method in mixed gas atmosphere of argon gas and oxygen gas is employed.

Then, the manufacturing apparatus performs annealing in the air at 300° C. for one hour. The specific dielectric constant of the thermal oxide film 10 is approximately 4, and the specific dielectric constant of the tantalum oxide (ion-sensitive insulating film 14) that is formed as a film through sputtering is approximately 20. The film thickness of the thermal oxide film 10 and ion-sensitive insulating film 14 is set at 200 nm, respectively. Accordingly, a difference in a value of the specific dielectric constant reflects on the electrostatic capacity per unit area, and thus the electrostatic capacity per unit area of the ion-sensitive insulating film 14 composed of the tantalum oxide is approximately five times larger than the electrostatic capacity per unit area of the gate insulating film constituted by the thermal oxide film 10.

Continuously, the manufacturing apparatus exposes the surface of the ion-sensitive insulating film 14 located directly over a channel region of the semiconductor active layer 12, and covers the remaining part of the surface of the ion-sensitive insulating film 14 with the protective insulating film 15. It is preferable that a silicone resin is used as the protective insulating film 15, but a photoresist, an epoxy resin, and the like may be used as long as appropriate water resistance and insulating properties are obtained.

The TFT having the structure described above is immersed in phosphate buffered saline that includes the sensing object material 16. At this time, the exposed region of the ion-sensitive insulating film 14 comes into contact with the phosphate buffered saline. Furthermore, the phosphate buffered saline is an example of the solution. In addition, an Ag/AgCl electrode that is filled with a saturated KCl solution is used as the reference electrode 17, and is immersed in the phosphate buffered saline that includes the sensing object material 16.

For example, a main component of the enzyme 19 is glucose oxidase. Specifically, the enzyme 19 is a mixed material of 10% glucose oxidase, 10% bovine serum albumin, and 8% glutaraldehyde. The manufacturing apparatus adds the enzyme 19 dropwise to one surface of the second insulating substrate 18, and dries the enzyme 19 at room temperature for two hours. Through the drying, the enzyme 19 is fixed to the second insulating substrate 18.

The enzyme 19 after the fixing is immersed in a phosphate buffer solution that is adjusted to pH 6.5 and 0.1 mol/L, and is kept at 4° C. The manufacturing apparatus immerses the second insulating substrate 18, to which the enzyme 19 is fixed, in the phosphate buffered saline that includes the sensing object material 16. Here, the second insulating substrate 18 faces the silicon substrate 11 on which the TFT is formed. At this time, the second insulating substrate 18 and the silicon substrate 11 may be bonded to each other with a spacer interposed therebetween so as to control a distance between two substrates. The phosphate buffered saline is adjusted to pH 6.8 and a liquid temperature of 37° C. as optimal environment of the enzyme 19.

In the TFT biosensor 101 that is configured as described above, first, the present inventors applied a constant potential of 0.5 V to the drain electrode 13d of the TFT biosensor 101, set the source electrode 13s and the reference electrode 17 to a ground potential (0 V), and changed a gate voltage Vg to vary in a range of 0 V to +7 V so as to measure Vg-Id characteristics (characteristics of a drain current Id to the gate voltage Vg).

Figure 2:
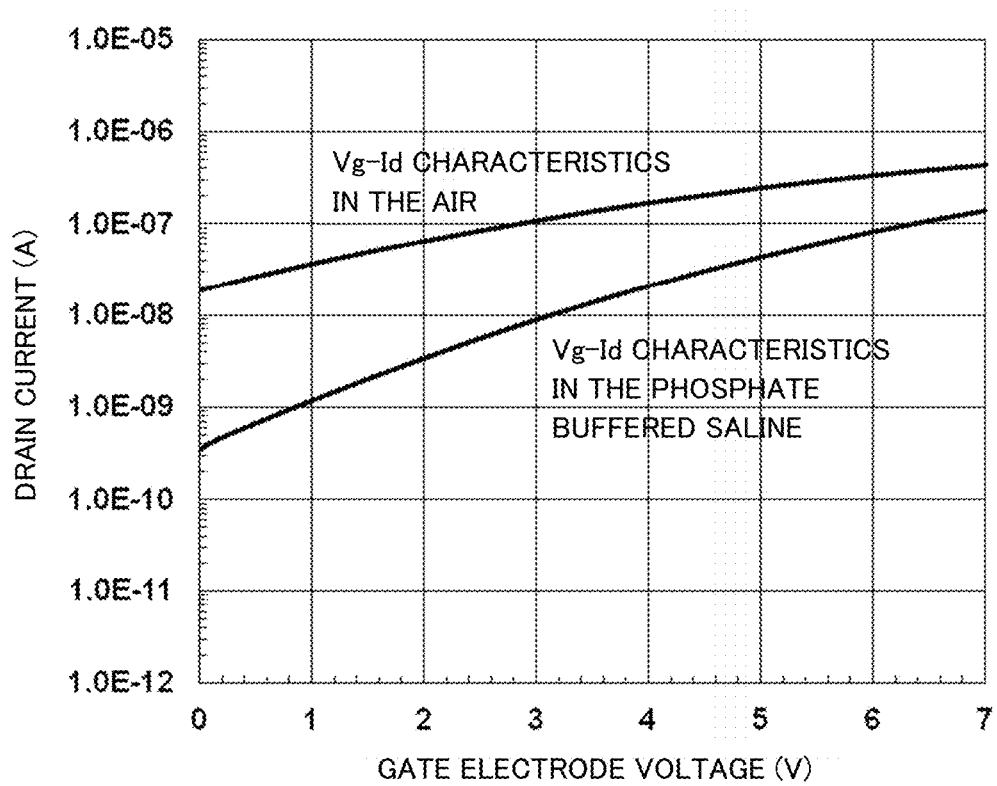
FIG. 2 is a graph illustrating Vg-Id characteristics of a TFT biosensor of Example 1.

FIG. 2 is a graph illustrating the Vg-Id characteristics of the TFT biosensor 101 of Example 1. A graph on an upper side of FIG. 2 represents a measurement result of the Vg-Id characteristics in the air, and a graph on a lower side represents a measurement result of the Vg-Id characteristics in the phosphate buffered saline. It can be understood that the Vg-Id characteristics shift to a positive side due to immersion in the liquid. Next, the present inventors added a glucose aqueous solution, which was adjusted in order for a final concentration to be a predetermined value, into the phosphate buffered saline. Furthermore, the TFT biosensor 101, the reference electrode 17, and the enzyme 19 fixed on the second insulating substrate 18 are immersed in the phosphate buffered saline. At this time, the added glucose is dissolved in the same phosphate buffered saline in order to keep pH of the phosphate buffered saline.

Here, the following reaction progresses between the glucose that is added and the glucose oxidase (enzyme 19).

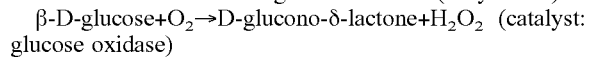
β-D-glucose+$O_2$→D-glucono-δ-lactone+$H_2O_2$ (catalyst: glucose oxidase)

At this time, D-glucono-δ-lactone is converted into a gluconic acid through hydrolysis, and pKa (acid dissociation constant) of the gluconic acid is approximately 3.8, and thus the pH variation of solution is caused. The pH variation increases in proportion to the concentration of glucose in the solution. Accordingly, the TFT biosensor 101 is possible to measure the concentration of glucose based on Vg-Id characteristic shift, which is caused by the pH variation.

In this example, a desired value is detected from Vth shift of the Vg-Id characteristics (the characteristics between the gate electrode voltage and the drain current). This is different from the related technologies such as the detection of interfacial potential or of ion concentration from Vth shift according to the Vref-Id characteristics.

The TFT biosensor 101 of Example 1 includes a detection unit that detects potential difference (corresponding to an electric double-layer potential that occurs at an interface), which occurs between the ion-sensitive insulating film 14 and the sensing object material 16, after amplifying the potential difference with a value of a ratio obtained by dividing the electrostatic capacity per unit area of the ion-sensitive insulating film 14 by the electrostatic capacity per unit area of the gate insulating film (thermal oxide film 10) when the sensing object material 16 is disposed on the ion-sensitive insulating film 14. For example, the detection unit reads out the potential difference obtained by multiplying the potential difference, which occurs on the ion-sensitive insulating film 14, by the value of the ratio of the electrostatic capacity. The maximum value of a variation in the electric double-layer potential to a variation in the concentration of hydrogen ions is 59 mV/pH. However, in Example 1, the value of the ratio obtained by dividing the electrostatic capacity per unit area of the ion-sensitive insulating film 14 by the electrostatic capacity per unit area of the gate insulating film (thermal oxide film 10) is greater than 1, and thus it is possible to realize sensitivity that is higher than 59 mV/pH. That is, the TFT biosensor 101 of Example 1 is the biosensor having pH sensitivity that is higher than 59 mV/pH.

In addition, the TFT biosensor 101 of Example 1 is biosensor including biomolecule recognition mechanism (for example, the enzyme 19) at spatially separated position from the ion-sensitive insulating film 14.

The meaning of the biomolecule recognition mechanism provided at the spatially separated position is that it can realize the high sensitivity bio-sensor described above without losing the configuration. When the biomolecule recognition mechanism is applied to the biopolymer fixed to the ion-sensitive film, it can be calculated that the pH sensitivity is determined by the value of ratio obtained by dividing an electrostatic capacity per unit area of the biopolymer that is fixed to the ion-sensitive film by the electrostatic capacity per unit area of the gate insulating film. Generally, the electrostatic capacity of the biopolymer is very smaller compared with the ion-sensitive insulating film. Therefore, in the case of fixing the biopolymer on the surface where the area between the detected liquid material and the ion-sensitive insulating film 14, it is difficult to realize the high sensitivity bio-sensor based on the principle of this embodiment.

In addition, it has the advantage caused by the independency of the pH measurement unit and the biological material recognition portion, because it brings the depression of interference between the pH measurement unit and the biological material recognition portion without the mutual function interference. In biological material recognition, it is possible to realize a large area and a large thickness of biopolymer fixing portion without inhibiting the pH measurement function, and it is possible to allow the enzyme reaction and molecule recognition reaction to efficiently progress. Accordingly, in the TFT biosensor 101 of Example 1, efficiency of the biomolecular recognition mechanism is realized while providing the interfacial potential detection function with high sensitivity. As a result, the TFT biosensor 101 can be applied to measurement of a low-concentration biological material.

In this example, the sensing is performed from the threshold voltage shift (Vth shift) of the characteristics of voltage which is applied to the gate electrode other than the reference electrode 17, to the drain current differently from the related technologies. In the case of using this detection method, when the electrostatic capacity per unit area of the ion-sensitive insulating film 14 is set to be greater than the electrostatic capacity per unit area of the gate insulating film (thermal oxide film 10), detection with sensitivity higher than Nernst limit is theoretically possible.

The effect of this example does not deny the Nernst theory, and is result of "amplification" caused by the electric double-layer potential difference, which occurs on the surface of the ion-sensitive insulating film 14 in accordance with the Nernst theory, through a mutual operation between a bottom gate electric field and a top gate electric field. The amplification effect is realized by setting the electrostatic capacity per unit area of the ion-sensitive insulating film 14 to be greater than the electrostatic capacity per unit area of the gate insulating film (thermal oxide film 10). This effect does not depend on amplification with an external circuit and is not influenced by various kinds of fluctuation, and thus intrinsic high sensitivity of the TFT biosensor 101 is realized. As a result, it is possible to solve the problem of the related technologies.

In this example, the description has been given of the example in which glucose oxidase is used as the enzyme 19, but there is no limitation thereto. Any enzyme reaction may be employed as long as a pH variation of solution is caused.

In addition, when activity of the enzyme 19 decreases, the initial activity of the enzyme 19 can be obtained again by replacing the second insulating substrate 18 and the enzyme 19 with new one while keeping a portion other than the substrate (second insulating substrate 18) of the enzyme 19. As a result, the lifetime of the entirety of the ion sensor is lengthened, and thus it is possible to provide as ion sensor that can be used with small burden for the user.

In addition, the function capable of replacing the second insulating substrate 18 and the enzyme 19 with new one is the same as a configuration in which substitution with another enzyme is possible. Due to this replacement function, it is possible to provide a biosensor capable of measuring other items with a single configuration.

The description has been given of the method of measuring the ion concentration in the sensing object material 16 from the threshold voltage shift of the Vg-Id characteristics. In addition to this, when the user reads the sensor current between the source and the drain measured by ammeter at the fixed gate-source voltage, the sensor can detect the changing in the ion concentration.

Here, InGaZnO is used as the semiconductor active layer 12, but there is no limitation thereto. For example, amorphous silicon, polysilicon, ZnO, InSnZnO, and the like can be used. In addition, it is preferable to use a wide bandgap semiconductor in which a free hole is less likely to be accumulated.

The ion-sensitive insulating film 14 is not limited to the tantalum (Ta) oxide, but it is preferable to use a material having a high specific dielectric constant. For example, in addition to the tantalum oxide ($TaO_2$), the material may be a hafnium oxide ($HfO_2$), an aluminum oxide ($Al_2O_3$), a barium titanate ($BaTiO_3$), a strontium titanate ($SrTiO_3$), a silicon nitride ($Si_3N_4$) film, and the like, and an arbitrary stacked film thereof is also possible. In addition, the gate insulating film is not limited to the silicon oxide, and may be a silicon nitride, an aluminum oxide, and the like, and an arbitrary staked film thereof is also possible.

As described above, the ion sensor of this embodiment can detect the electric double-layer potential, which occurs on the surface of the ion-sensitive insulating film 14, after amplification thereof. Accordingly, it is possible to detect a minute variation in the concentration of hydrogen ions, that is, the pH variation. In addition, it is possible to increase the amount of enzyme per unit area of the pH sensing portion. Accordingly, it is possible to make the amount of pH variation due to the enzyme reaction large, and thus it is possible to raise detection sensitivity for the biological material.

(Second Embodiment)

Figure 3:
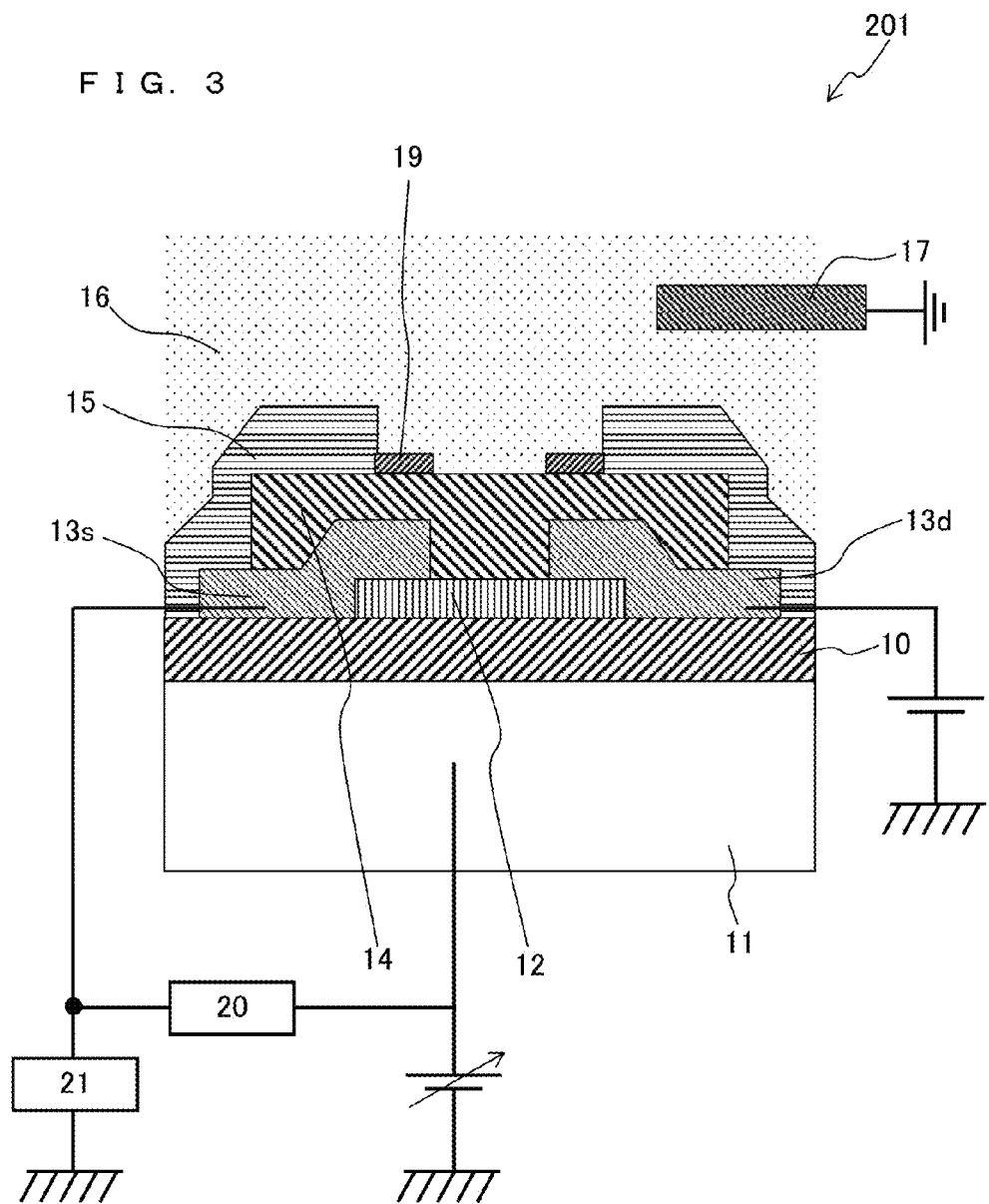
FIG. 3 is a cross-sectional view illustrating a TFT biosensor of second embodiment.

FIG. 3 is a cross-sectional view illustrating a TFT biosensor 201 of second embodiment.

As is the case with the TFT biosensor 101 of the first embodiment, the TFT biosensor 201 of the second embodiment includes the semiconductor active layer 12 to which the source electrode 13s and the drain electrode 13d are connected. In addition, a thermal oxide film 10 as a gate insulating film, and a silicon substrate 11 as a gate electrode are provided on one surface (a first surface, a lower surface in FIG. 3) of the semiconductor active layer 12. In addition, an ion-sensitive insulating film 14 and a protective insulating film 15 are provided on the other surface (a second surface, an upper surface in FIG. 3) of the semiconductor active layer 12. In addition, the TFT biosensor 201 includes a reference electrode 17 at the spatially separated position from the ion-sensitive insulating film 14 and the protective insulating film 15. Furthermore, the electrostatic capacity per unit area of the ion-sensitive insulating film 14 is set to be greater than the electrostatic capacity per unit area of the gate insulating film (the thermal oxide film 10). In addition, in the TFT biosensor 201, in a region, which is not covered with the protective insulating film 15, on a surface (upper surface) of the ion-sensitive insulating film 14, the enzyme 19 is fixed to a portion other than a portion located directly over a region in which a lower surface of the ion-sensitive insulating film 14 comes into contact with the semiconductor active layer 12.

In addition, the TFT biosensor 201 further includes any one of the voltage detection unit 20 that reads out potential difference between the source electrode 13s and the gate electrode (silicon substrate 11), and the current detection unit 21 that reads out a current that flows to the source electrode 13s or the drain electrode 13d. Furthermore, in FIG. 3, both the voltage detection unit 20 and the current detection unit 21 are illustrated in the drawing.

(Example 2)

Figure 4:
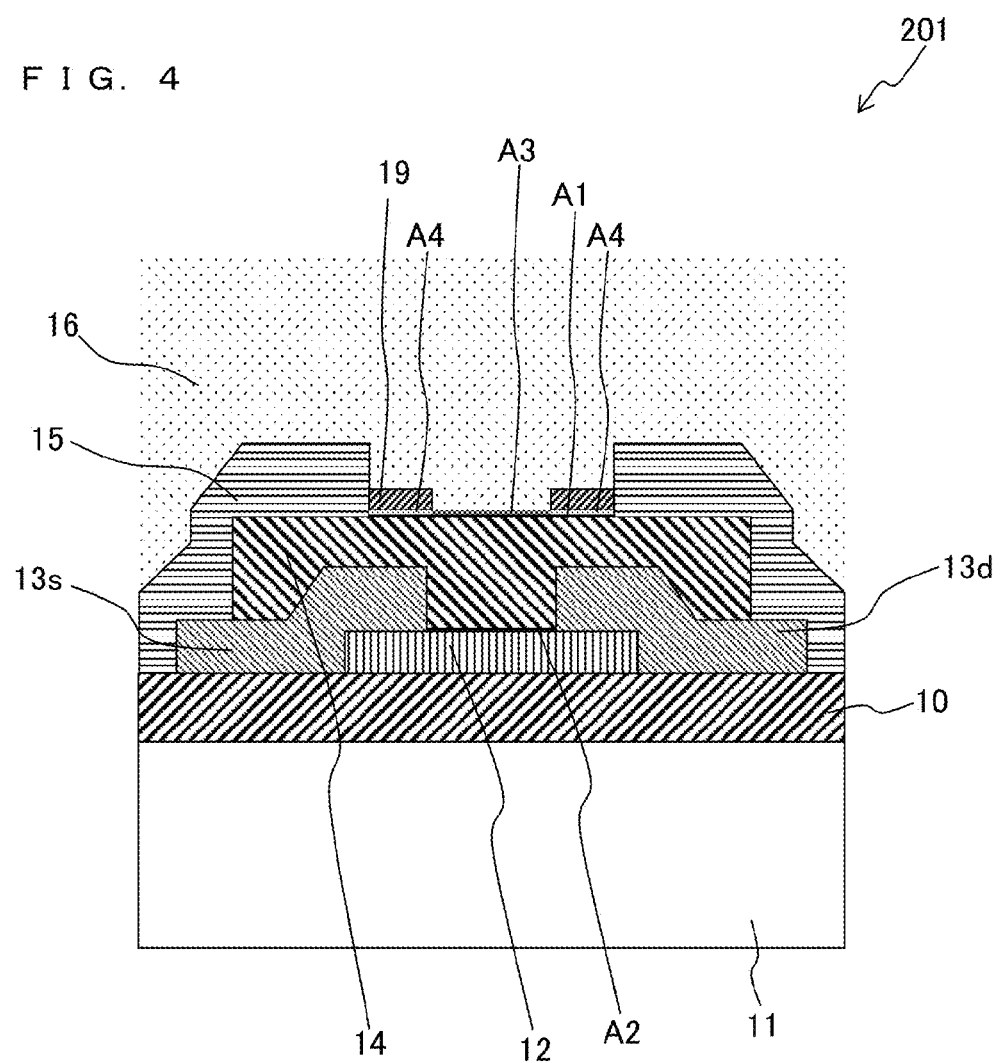
FIG. 4 is a schematic view of a part of the TFT biosensor in FIG. 3.
Figure 5:
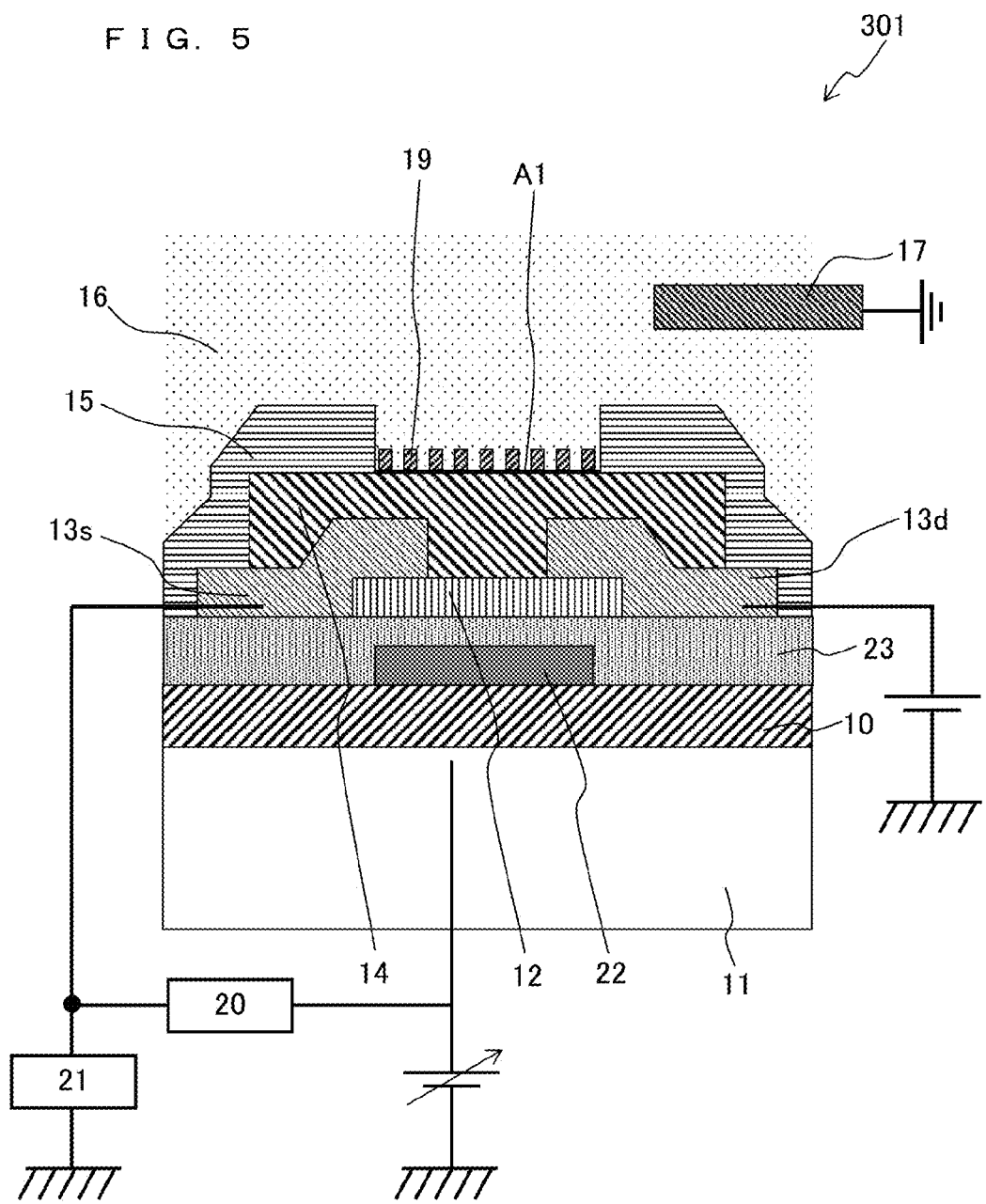
FIG. 5 is a cross-sectional view illustrating a TFT biosensor of Example 3.

Next, Example 2, which further specifies the second embodiment, is described using FIGS. 3 and 4. FIG. 4 is a schematic view of a part of the TFT biosensor 201 in FIG. 3. Reference numerals A1 to A4 in FIGS. 4 and 5 are reference numerals which indicate regions, and are not reference numerals which indicate a material (such as the semiconductor active layer 12, the ion-sensitive insulating film 14, the enzyme 19, and the like).

In the TFT biosensor 201 of Example 2, the thermal oxide film 10 is formed on the silicon substrate 11 in the film thickness of 200 nm. A silicon oxide film, a silicon nitride film, and the like, which are formed by plasma chemical vapor deposition (CVD) method or sputtering method, may be used instead of the thermal oxide film 10.

An oxide semiconductor film composed of In—Ga—Zn—O and having the film thickness of 50 nm is deposited on the silicon substrate 11 covered with the thermal oxide film 10 by sputtering method. The oxide semiconductor film is patterned by the photo-resist process, and is etched by oxalic acid to form the semiconductor active layer 12 having a predetermined island shape. After formation of the semiconductor active layer 12, the substrate is annealed in the air at 400° C. for one hour.

Continuously, the titanium film is deposited by DC sputtering method, and the pattern is formed by photoresist process. And then, it is etched by using fluorine gas-based plasma (for example, $SF_6$ or $CF_4$) to form the source electrode 13s and the drain electrode 13d. At this time, In—Ga—Zn—O is not etched with the fluorine gas-based plasma, and thus it is possible to obtain a desired electrode shape without forming an etch-stop layer. Furthermore, the film thickness of the source electrode 13s and the drain electrode 13d is set at 50 nm, respectively.

Next, the ion-sensitive insulating film 14 composed of hafnium oxide ($HfO_2$) with film thickness of 200 nm, is deposited by sputtering method by using metal mask. In the film sputtering process, the sintered Hf—O target is used, the substrate is not heated, and RF sputtering method in a mixed gas atmosphere of argon gas and oxygen gas is employed. And then, the substrate is annealed in the air at 300° C. for one hour. Furthermore, the upper surfaced of the semiconductor active layer 12 comes into the ion-sensitive insulating film 14 at a region (a second region A2 in FIG. 4) in which the source electrode 13s and the drain electrode 13d are not formed.

A specific dielectric constant of the thermal oxide film 10 is approximately 4, and a specific dielectric constant of the hafnium oxide (ion-sensitive insulating film 14) that is formed as film through sputtering is around 20. The film thickness of the thermal oxide film 10 and ion-sensitive insulating film 14 is 200 nm, respectively. Accordingly, a difference in the specific dielectric constant reflects on the electrostatic capacity per unit area, and thus the electrostatic capacity per unit area of the ion-sensitive insulating film 14 composed of the hafnium oxide is approximately five times larger than the electrostatic capacity per unit area of the gate insulating film constituted by the thermal oxide film 10.

Then, the surface (a first region A1 in FIG. 4) of the ion-sensitive insulating film 14 located directly over the channel region of the semiconductor active layer 12 is exposed, and the surface of the peripheral edge portion is covered with the protective insulating film 15 except for the first region A1. A polyimide resin is used as the protective insulating film 15. The first region A1 includes a region (a third region A3 in FIG. 4) located directly over the second region A2 in which the semiconductor active layer 12 and the ion-sensitive insulating film 14 come into contact with each other, and is formed to be greater than the second region A2. Next, the manufacturing apparatus fixes glucose dehydrogenase 19 to a fourth region A4 excluding the third region A3 in the first region A1 of the ion-sensitive insulating film 14. Protein including the glucose dehydrogenase 19 has a property of being adsorbed to an oxide such as glass in a non-specific manner.

Therefore, the manufacturing apparatus adds an enzyme aqueous solution dropwise to a target portion (the fourth region A4 of the ion-sensitive insulating film 14) and dries the enzyme aqueous solution. According to this, the enzyme 19 is easily fixed to the target portion. In addition, for strong fixing of the enzyme 19, it is preferable to insert a self-assembled monolayer (SAM) film as a linker. Examples of a method of forming the SAM film include spin coating, dip coating, and vacuum deposition, but there is no limitation thereto. As a material of the SAM film, a material that modifies a surface through a tiol group, or a silane coupling agent can be used. However, there is no limitation thereto as long as appropriate coupling strength is obtained.

As described above, in the ion-sensitive insulating film 14, the peripheral edge portion other than the first region A1 is covered with the protective insulating film 15. The second surface (upper surface in FIG. 4) of the semiconductor active layer 12 includes the second region A2 that comes into contact with the ion-sensitive insulating film 14. The first region A1 includes the third region A3 that overlaps with the second region A2, and the fourth region A4 other than the third region A3. The enzyme 19 is fixed to the fourth region A4. The ion-sensitive insulating film 14 comes into contact with the solution in the third region A3.

The fourth region A4 is located on the source electrode and the drain electrode of the TFT, and thus potential variation in the fourth region A4 does not have an effect on sensitivity. Accordingly, it is possible to effectively use the fourth region A4, which does not effect on the sensitivity, as the region of the enzyme 19.

(Example 3)

Next, Example 3 as a modification example of the second embodiment is described using FIG. 5. FIG. 5 is a cross-sectional view illustrating a TFT biosensor 301 of Example 3.

In the TFT biosensor 301 of Example 3, the thermal oxide film 10 is formed on the silicon substrate 11 in a film thickness of 200 nm. Next, a metallic chromium film is formed by DC sputtering method using metal mask, and the film is patterned to form a first gate electrode 22. Continuously, a silicon oxide film is formed in the mixed atmosphere of argon gas and oxygen gas by RF sputtering method using metal mask in order to form a first gate insulating film 23. In the film formation, any one of a silicon oxide and a metallic silicon may be used as a target, and a desired withstand pressure is obtained by appropriately controlling an oxygen partial pressure.

In addition, the oxide semiconductor film composed of In—Ga—Zn—O and having the film thickness of 50 nm is sputtered on the first gate insulating film 23 using metal mask in order to form the semiconductor active layer 12. After formation of the semiconductor active layer 12, the annealing process is performed in the air at 400° C. for one hour. Continuously, the source electrode 13s and the drain electrode 13d are formed by DC-sputtering of aluminum using metal mask. Furthermore, the film thickness of the source electrode 13s and the drain electrode 13d is set at 100 nm, respectively.

In addition, the ion-sensitive insulating film 14 composed of tantalum oxide ($TaO_2$) and having the film thickness of 200 nm is sputtered by using metal mask. In the film formation process, a sintered body target composed of Ta—O is used, the substrate is not heated, and RF sputtering method in a mixed gas atmosphere of argon gas and oxygen gas is employed. Then, the annealing process is performed in the air at 300° C. for one hour. A specific dielectric constant of the thermal oxide film 10 is approximately 4, and a specific dielectric constant of the tantalum oxide (ion-sensitive insulating film 14) that is formed as a film through sputtering is approximately 20. The film thickness of the thermal oxide film 10 and ion-sensitive insulating film 14 is 200 nm, respectively. Accordingly, a difference in the specific dielectric constant reflects on the electrostatic capacity per unit area, and thus the electrostatic capacity per unit area of the ion-sensitive insulating film 14 composed of the tantalum oxide is approximately five times larger than the electrostatic capacity per unit area of the gate insulating film constituted by the thermal oxide film 10.

Then, the surface (the first region A1) of the ion-sensitive insulating film 14 located directly over the channel region of the semiconductor active layer 12 is exposed, and the protective insulating film 15 covers it except for the first region A1. A silicone resin is used as the protective insulating film 15, but an inorganic insulating material such as alumina may be used as long as appropriate water resistance and insulating properties are secured.

Continuously, the manufacturing apparatus adds an enzyme aqueous solution dropwise onto the first region A1 of the ion-sensitive insulating film 14 by using a dispenser, and dries the enzyme aqueous solution at room temperature. According to this, the enzyme 19 is fixed onto the first region A1 of the ion-sensitive insulating film 14. For example, the enzyme 19 is provided on the first region A1 with a regular interval or in a random manner. At this time, it is important that the ion-sensitive insulating film 14 is appropriately exposed, and contact between the ion-sensitive insulating film 14 and the sensing object material 16 is secured. As a result, it is possible to provide a TFT biosensor in which both the biological material recognition mechanism and the pH sensing mechanism are provided on the ion-sensitive insulating film 14 without the mutual functional interference.

As is the case with the TFT biosensor 101 of Example 1, in the TFT biosensor 201 of Example 2 and the TFT biosensor 301 of Example 3, the Vg-Id characteristics as illustrated in FIG. 2 is also obtained. Accordingly, it is possible to perform sensing from the threshold voltage shift of Vg-Id characteristics. In addition, even in Examples 2 and 3, the TFT biosensors 201 and 301 are provided with a detection unit that detects potential difference, which occurs between the ion-sensitive insulating film 14 and the sensing object material 16, after amplifying the potential difference by multiplying the potential difference by the value of the ratio obtained by dividing the electrostatic capacity per unit area of the ion-sensitive insulating film 14 by the electrostatic capacity per unit area of the gate insulating film (thermal oxide film 10). According to this, it is possible to realize the biosensor having high pH sensitivity.

(Third Embodiment)

Figure 6:
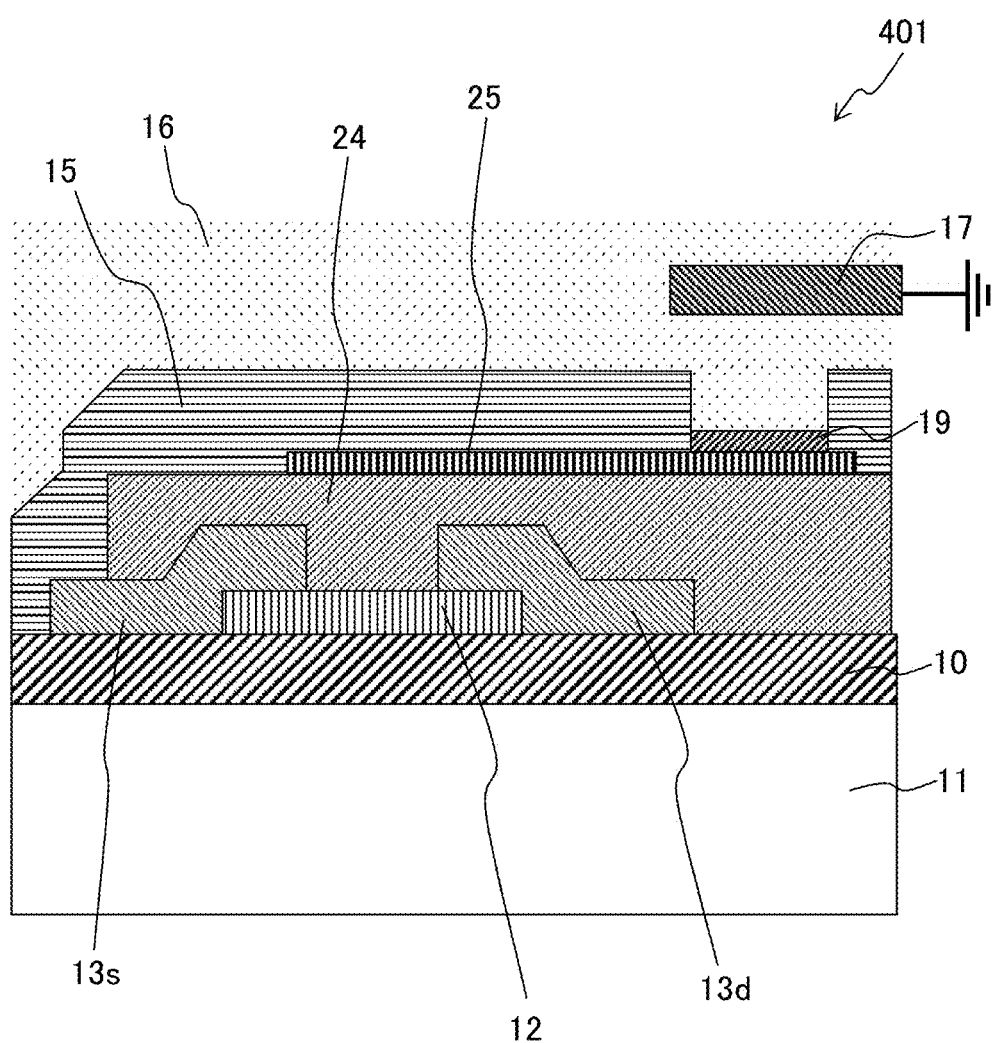
FIG. 6 is a cross-sectional view illustrating a TFT biosensor of third embodiment.

FIG. 6 is a cross-sectional view illustrating a TFT biosensor 401 of third embodiment.

The TFT biosensor 401 of the third embodiment includes the semiconductor active layer 12 to which the source electrode 13s and the drain electrode 13d are connected. The thermal oxide film 10 as the first gate insulating film and the silicon substrate 11 as the first gate electrode are provided on one surface (a first surface, a lower surface in FIG. 6) of the semiconductor active layer 12. A second gate insulating film 24 and a second gate electrode 25 are provided on the other surface (a second surface, an upper surface in FIG. 6) of the semiconductor active layer 12.

An electrostatic capacity per unit area of the second gate insulating film 24 is set to be greater than the electrostatic capacity per unit area of the first gate insulating film (thermal oxide film 10). The second gate electrode 25 includes a region, which overlaps with the semiconductor active layer 12, on an upper surface of the second gate insulating film 24, and is disposed to two-dimensionally (to a right direction in FIG. 6) extend from the region. That is, the second gate electrode 25 is provided on the second gate insulating film 24, and extends from the region, which overlaps the semiconductor active layer 12, to a position that is two-dimensionally separated from the region.

In addition, in the second gate electrode 25, the enzyme 19 is fixed to an upper surface on an extension end side, and a region other than the region, to which the enzyme 19 is fixed, is covered with the protective insulating film 15. The enzyme 19 reacts with a material in the solution and modulates a voltage that is applied to the second gate electrode 25.

In addition, the TFT biosensor 401 includes the reference electrode 17 at the spatially separated position from the enzyme 19 that is fixed onto the second gate electrode 25, and the protective insulating film 15. A sensing object material 16 that is included in the solution is disposed on the second gate electrode 25 and the enzyme 19, and a voltage form the reference electrode 17 is applied to the second gate electrode 25. At this time, an effective gate voltage, which is applied to the TFT biosensor 401, becomes a value obtained by adding a redox potential of enzyme reaction, which progresses on the second gate insulating film 24, to the voltage of the reference electrode 17, and a top channel, which is caused by the effective gate voltage, is induced to the semiconductor active layer 12.

At this time, the TFT biosensor 401 is driven by the silicon substrate 11 that becomes the first gate electrode, and the voltage of the reference electrode 17 is kept to be constant. According to this, it is possible to detect the redox potential, which is caused by reaction of the enzyme 19 with a substrate, as the Vth shift of Vref-Id characteristics.

As is the case with Example 3, when the enzyme 19 is intermittently disposed on the ion-sensitive insulating film 14, it is possible to increase an effective surface area of the enzyme 19, and contact between the ion-sensitive insulating film 14 and the sensing object material 16 is secured. As a result, a sensitivity improving effect is obtained.

(Example 4)

Next, Example 4, which further specifies the third embodiment, is described using FIG. 6.

In the TFT biosensor 401 of Example 4, the thermal oxide film 10 is formed on the silicon substrate 11 in the film thickness of 200 nm. A silicon oxide film, a silicon nitride film, and the like, which are formed by plasma CVD method or sputtering method, may be used instead of the thermal oxide film 10.

In addition, the oxide semiconductor film composed of In—Ga—Zn—O and having the film thickness of 50 nm is formed on the silicon substrate 11 covered with the thermal oxide film 10 by sputtering method using metal mask. In the film formation, the sintered In—Ga—Zn—O target is used, the substrate is not heated, and DC sputtering method in a mixed gas atmosphere of argon gas and oxygen gas is employed. After the film formation, the annealing process is performed in the air at 400° C. for one hour. The semiconductor active layer 12 having an island shape is formed by patterning the oxide semiconductor film.

Continuously, the aluminum metal, or the aluminum metal that contains 1% of silicon is DC-sputtered by using metal mask in order to form the source electrode 13s and the drain electrode 13d. The film thickness of the source electrode 13s and the drain electrode 13d is set at 50 nm, respectively. In addition, the second gate insulating film 24 composed of aluminum oxide and having the film thickness of 200 nm is formed by sputtering method using metal mask. In the film formation, when a ratio of the argon gas and oxygen gas is appropriately controlled, it is possible to use both a sintered body target composed of Al—O, and a metallic aluminum target. The substrate is not heated, and RF sputtering method is employed.

Then, the second gate electrode 25 composed of tungsten (W) metal and having the film thickness of 50 nm is formed by sputtering method using metal mask. In addition, the annealing process is performed in the air at 300° C. for one hour, and the protective insulating film 15 covers the second gate electrode 25 except for a part thereof. Furthermore, in the second gate electrode 25, a predetermined region (refer to a right side in the drawing), which is opposite to a site that overlaps with the semiconductor active layer 12, is exposed, and a region other than the predetermined region is covered with the protective insulating film 15. It is preferable that a silicone resin is used as the protective insulating film 15, but a photoresist, an epoxy resin, and the like may be used as long as appropriate water resistance and insulating properties are obtained.

Next, the manufacturing apparatus adds a glucose dehydrogenase aqueous solution dropwise to the region of the second gate electrode 25 which is not covered with the protective insulating film 15, and dries the aqueous solution at room temperature for solidification. According to this, the enzyme 19 is fixed onto the second gate electrode 25. In this example, the glucose dehydrogenase is used as the enzyme 19. However, there is no limitation thereto, and it is possible to employ other combinations of enzyme and a substrate as long as a redox reaction progresses on the second gate electrode 25.

In addition, the enzyme 19 is also not limited to a so-called enzyme, and a reaction between biomolecules, through which potential variation occurs on the second gate electrode 25, may be applied as the sensing object material 16 and the enzyme 19 in this example. For example, application can be expanded to antigen-antibody reaction, coupling of lectin and physiological active sugar chain, a mutual operation of DNA-DNA or RNA-RNA, and coupling between inorganic compounds.

In the configuration of Example 4, the region over the TFT channel is covered with the protective insulating film 15, and thus it is possible to suppress intrusion of the sensing object material 16 (a test liquid, and the like) to the channel portion. As a result, reliability is improved.

(Fourth Embodiment)

Figure 7:
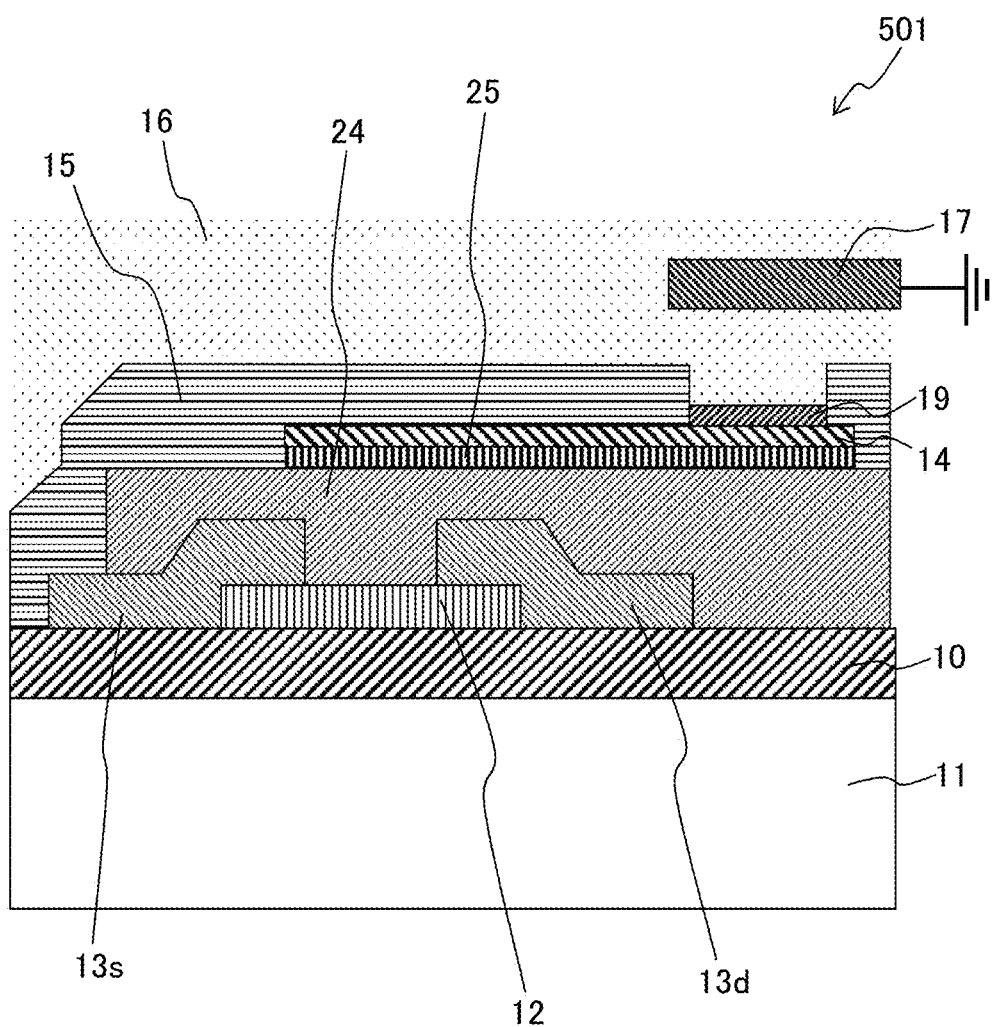
FIG. 7 is a cross-sectional view illustrating a TFT biosensor of fourth embodiment.

FIG. 7 is a cross-sectional view illustrating a TFT biosensor 501 of fourth embodiment.

The TFT biosensor 501 of the fourth embodiment includes the semiconductor active layer 12 to which the source electrode 13s and the drain electrode 13d are connected. The thermal oxide film 10 as the first gate insulating film and the silicon substrate 11 as the first gate electrode are provided on one surface (a first surface, a lower surface in FIG. 7) of the semiconductor active layer 12. The second gate insulating film 24, the second gate electrode 25, and the ion-sensitive insulating film 14 are provided on the other surface (a second surface, an upper surface in FIG. 7) of the semiconductor active layer 12. The electrostatic capacity per unit area of the second gate insulating film 24 is set to be greater than the electrostatic capacity per unit area of the first gate insulating film (the thermal oxide film 10).

The second gate electrode 25 includes a region, which overlaps with the semiconductor active layer 12, on the upper surface of the second gate insulating film 24, and is disposed to two-dimensionally (to a right direction in FIG. 7) extend from the region. That is, the second gate electrode 25 is provided on the second gate insulating film 24, and extends from the region, which overlaps the semiconductor active layer 12, to a position that is two-dimensionally separated from the region.

The ion-sensitive insulating film 14 is provided on the upper surface of the second gate electrode 25. In addition, in the ion-sensitive insulating film 14, the enzyme 19 is fixed to the upper surface in a region that is opposite to the region that overlaps with the semiconductor active layer 12, and a region other than the region, in which the enzyme 19 is fixed, is covered with the protective insulating film 15. The TFT biosensor 501 includes the reference electrode 17 at the spatially separated position from the enzyme 19 that is fixed onto the ion-sensitive insulating film 14, and the protective insulating film 15. The sensing object material 16 is disposed on the ion-sensitive insulating film 14 and the enzyme 19, and the voltage from the reference electrode 17 is applied to the second gate electrode 25. The potential variation, which occurs through the reaction of enzyme 19, is superimposed on the potential of the reference electrode 17, this potential is transmitted to the second gate electrode 25, and induces a top channel in the semiconductor active layer 12 through the second gate insulating film 24.

At this time, the TFT biosensor 501 is driven by the silicon substrate 11 that becomes the first gate electrode, and the potential of the reference electrode 17 is kept to be constant. According to this, it is possible to detect the potential, which is caused by the reaction of enzyme 19 with the substrate, as the Vth shift of the Vref-Id characteristics.

(Example 5)

Next, Example 5, which further specifies the fourth embodiment, is described using FIG. 7.

In the TFT biosensor 501 of Example 5, the semiconductor active layer 12, the source electrode 13s and drain electrode 13d, the second gate insulating film 24, the second gate electrode 25, and the ion-sensitive insulating film 14 are formed in this order on the silicon substrate 11 covered with the thermal oxide film 10 by sputtering method using metal mask. The semiconductor active layer 12 is composed of In—Ga—Zn—O and has the film thickness of 50 nm. The source electrode 13s and the drain electrode 13d are composed of molybdenum metal and have the film thickness of 100 nm. The second gate insulating film 24 is composed of tantalum oxide and has the film thickness of 100 nm. The second gate electrode 25 is composed of molybdenum metal and has the film thickness of 50 nm. The ion-sensitive insulating film 14 is composed of silicon oxide and has the film thickness of 100 nm.

At this time, the materials of the respective layers are not limited to the above-described materials, and titanium (Ti), aluminum (Al), tungsten (W), tantalum (Ta), chromium (Cr), and an alloy film thereof, or a stacked film thereof can be used as the electrodes. In addition, aluminum oxide, silicon nitride ($Si_3N_4$), zirconium oxide ($ZrO_2$), hafnium oxide, strontium titanate ($SrTiO_3$), barium titanate ($BaTiO_3$), and a stacked film thereof can be used as the insulating films.

In addition, the annealing process is performed in the air at 300° C. for one hour, and the protective insulating film 15 composed of silicone resin covers the ion-sensitive insulating film 14 except for a part thereof. In addition, in the ion-sensitive insulating film 14, a predetermined region (refer to a right side in the drawing), which is opposite to a site that overlaps with the semiconductor active layer 12, is exposed, and a region other than the predetermined region is covered with the protective insulating film 15.

Next, the manufacturing apparatus adds the phosphate buffer solution set to pH 6.8 in which galectin as lectin that recognizes galactose in a specific manner is dissolved, dropwise to the region of the ion-sensitive insulating film 14 which is not covered with the protective insulating film 15, and dries the phosphate buffer solution in room temperature for solidification. According to this, the enzyme 19 is fixed to the ion-sensitive insulating film 14. The enzyme 19 is coupled to galactose in the specific manner, and allows the interfacial potential of the ion-sensitive insulating film 14 to vary.

It is possible to measure galactose by detecting the potential variation with the TFT sensor. Here, galectin is used as lectin, but there is no limitation thereto. When using lectin having different substrate-specificity, it is possible to provide a TFT biosensor in which a different physiological active sugar chain is set as an object.

In example 5, the ion-sensitive insulating film 14 is further provided between the enzyme 19 and the second gate electrode 25, compared with Example 4. When the insulating film 14 exists, it is possible to suppress electrical short-circuiting between the sensing object material 16 and the second gate electrode 25, and thus it is possible to further improve reliability.

(Example 6)

Figure 8:
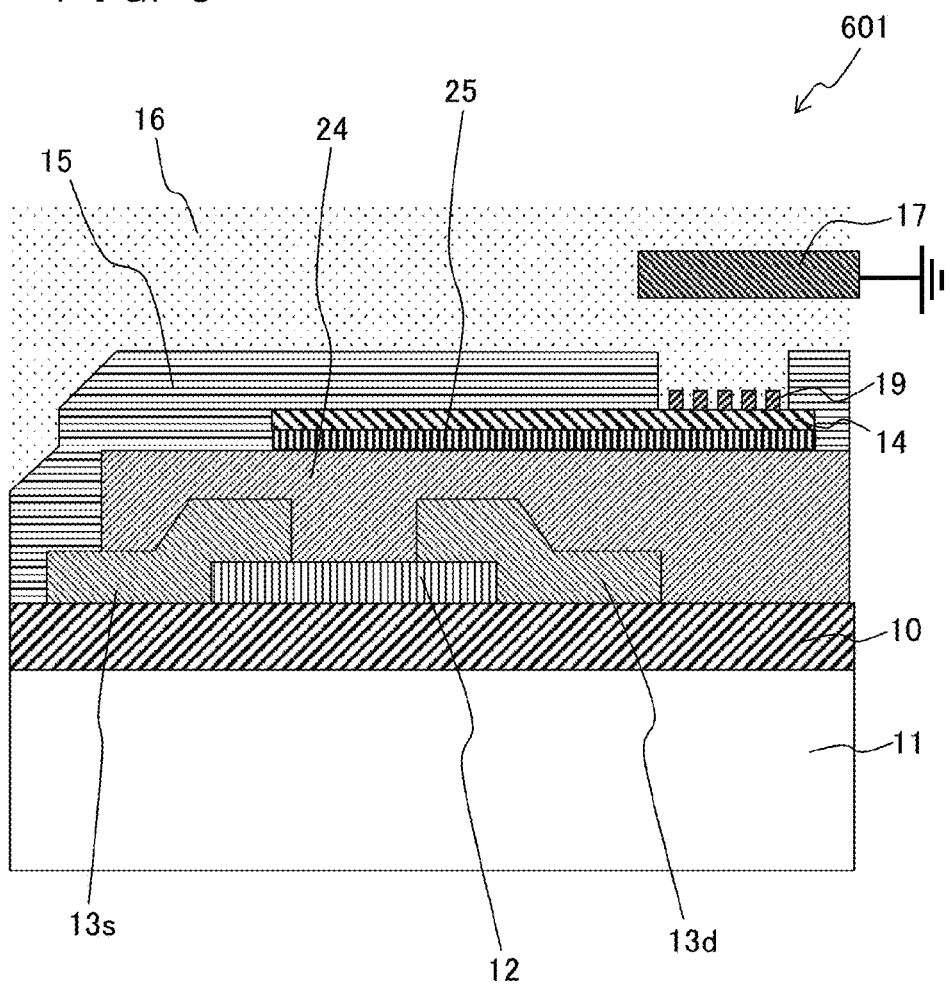
FIG. 8 is a cross-sectional view illustrating a TFT biosensor of Example 6.

Next, Example 6, which is a modification example of the fourth embodiment, is described using FIG. 8. FIG. 8 is a cross-sectional view illustrating a TFT biosensor 601 of Example 6.

As is the case with Example 5, the TFT biosensor 601 of Example 6 has the structure in which the semiconductor active layer 12, the source electrode 13s and the drain electrode 13d, the second gate insulating film 24, the second gate electrode 25, and the ion-sensitive insulating film 14 are stacked on the silicon substrate 11 on which the thermal oxide film 10 is formed. As manufacturing means, a sputtering method that uses a metal mask may be applied, or a photolithography method may be used.

Next, the photoresist is patterned on the ion-sensitive insulating film 14. As the photoresist that is used at this time, a lift-off dedicated resist is preferable, but any resist may be used as long as the resist can be easily removed with an organic solvent such as acetone. In addition, the manufacturing apparatus applies a phosphate buffer solution set to pH 6.8, in which alcohol dehydrogenase is dissolved, onto the photoresist that is patterned. As an application method, spin coating, dipping, and potting may be selected in accordance with viscosity of the solution. Then, the manufacturing apparatus removes the photoresist, which is patterned, with acetone to form the enzyme 19 that is patterned. The enzyme 19 is provided in a predetermined region of the ion-sensitive insulating film 14 with a regular interval or in a random manner.

Continuously, the protective insulating film 15 composed of silicone resin covers the ion-sensitive insulating film 14 except for a region in which the enzyme 19 is patterned. Through the above-described processes, it is possible to provide the TFT biosensor 601 in which the TFT is used as the interfacial potential detection mechanism and alcohol dehydrogenase is used as the biomolecule recognition mechanism, and which is capable of measuring an alcohol concentration.

Compared with Example 5, the enzyme 19 is intermittently disposed on the ion-sensitive insulating film 14, and thus it is possible to increase the effective surface area of the enzyme 19, and the contact between the ion-sensitive insulating film 14 and the sensing object material 16 is secured in Example 6 as same as in Example 3. As a result, a sensitivity improving effect is obtained.

(Fifth Embodiment)

Figure 9:
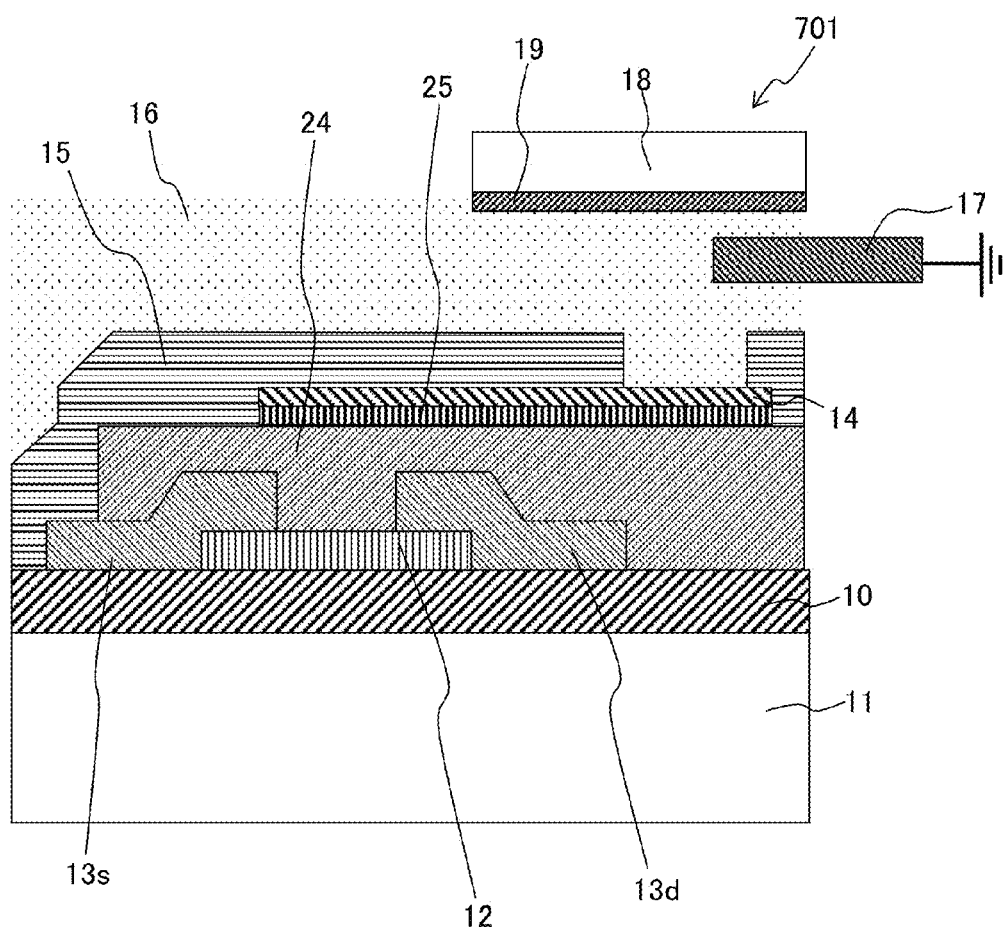
FIG. 9 is a cross-sectional view illustrating a TFT biosensor of fifth embodiment.

FIG. 9 is a cross-sectional view illustrating a TFT biosensor 701 of fifth embodiment.

The TFT biosensor 701 of the fifth embodiment includes the semiconductor active layer 12 to which the source electrode 13s and the drain electrode 13d are connected. The thermal oxide film 10 as the first gate insulating film and the silicon substrate 11 as the first gate electrode are provided on one surface (a first surface, a lower surface in FIG. 9) of the semiconductor active layer 12. The second gate insulating film 24, the second gate electrode 25, and the ion-sensitive insulating film 14 are provided on the other surface (a second surface, an upper surface in FIG. 9) of the semiconductor active layer 12.

The electrostatic capacity per unit area of the second gate insulating film 24 is set to be greater than the electrostatic capacity per unit area of the first gate insulating film (thermal oxide film 10). Furthermore, the position of the second gate electrode 25 and the ion-sensitive insulating film 14 with respect to the upper surface of the second gate insulating film 24 is the same as in Examples 5 and 6. In addition, in the ion-sensitive insulating film 14, the predetermined region (refer to a right side in the drawing), which is opposite to a region that overlaps with the semiconductor active layer 12, is exposed, and a region other than the predetermined region is covered with the protective insulating film 15.

In addition, the TFT biosensor 701 of the fifth embodiment includes the enzyme 19 fixed to a second insulating substrate 18 at a position spatially separated from the ion-sensitive insulating film 14. In addition, the TFT biosensor 701 includes the reference electrode 17 at a space between the ion-sensitive insulating film 14 and the enzyme 19. In the TFT biosensor 701 of the fifth embodiment, in a case where the sensing object material 16 is disposed on the ion-sensitive insulating film 14, the enzyme 19 reacts with the sensing object material 16, and causes the pH variation in the vicinity. It is possible to measure the concentration of the sensing object material 16 by grasping the pH variation as potential variation on the surface of the ion-sensitive insulating film 14.

(Example 7)

Next, Example 7, which further specifies the fifth embodiment, is described using FIG. 9.

In the TFT biosensor 701 of Example 7, the semiconductor active layer 12, the source electrode 13s and drain electrode 13d, the second gate insulating film 24, the second gate electrode 25, and the ion-sensitive insulating film 14 are formed on the silicon substrate 11 covered with the thermal oxide film 10 by sputtering method, and are patterned by photolithography method, respectively. The semiconductor active layer 12 is composed of In—Ga—Zn—O and has the film thickness of 30 nm. The source electrode 13s and the drain electrode 13d are composed of molybdenum metal and have the film thickness of 50 nm, respectively. The second gate insulating film 24 is composed of tantalum oxide and has the film thickness of 100 nm. The second gate electrode 25 is composed of molybdenum metal and has the film thickness of 50 nm. The ion-sensitive insulating film 14 is composed of silicon oxide and has the film thickness of 50 nm.

Continuously, the annealing process is performed in the air at 300° C. for one hour, and the protective insulating film 15 composed of silicone resin covers the ion-sensitive insulating film 14 except for a part thereof.

Then, the manufacturing apparatus fixes urease that becomes the enzyme 19 on the second insulating substrate 18. As fixing means, as described above, the method such as spin coating, dipping, and potting of an enzyme aqueous solution can be used. The urease is enzyme that hydrolyzes urea to generate ammonia and carbon dioxide, and pH in the vicinity of the urease varies toward an alkaline side due to generation of ammonia. It is possible to measure the urea concentration by grasping the variation with the TFT sensor. As described above, it is possible to provide the TFT biosensor 701 capable of measuring the urea concentration.

As is the case with the TFT biosensor 101 of Example 1, the biosensor 701 of Example 7 includes the biomolecule recognition mechanism (enzyme 19) at the spatially separated position from the ion-sensitive insulating film 14. Accordingly, it is possible to suppress the mutual function interference of the pH measurement unit and the biological material recognition mechanism. In addition, in a case where the enzyme 19 is inactivated, it is possible to replace a substrate of the enzyme 19 with new one while keeping a portion other than the substrate (the second insulating substrate 18) of the enzyme 19.

Even in Examples 5 to 7, as is the case with the TFT biosensor 401 of Example 4, the TFT biosensors 501 to 701 are driven by the silicon substrate 11 that becomes the first gate electrode, and the voltage of the reference electrode 17 is kept to be constant. According to this, it is possible to detect the redox potential, which is caused by the reaction of enzyme 19 with the substrate, as the Vth shift of Vref-Id characteristics. In addition, even in Examples 5 to 7, the TFT biosensors 501 to 701 are provided with a detection unit that detects potential difference, which occurs between the ion-sensitive insulating film 14 and the sensing object material 16, after amplifying the potential difference by multiplying the potential difference by the value of the ratio obtained by dividing the electrostatic capacity per unit area of the second gate insulating film 24 by the electrostatic capacity per unit area of the first gate insulating film (thermal oxide film 10). According to this, it is possible to realize the biosensor having high sensitivity.

(Sixth Embodiment)

Figure 10A:
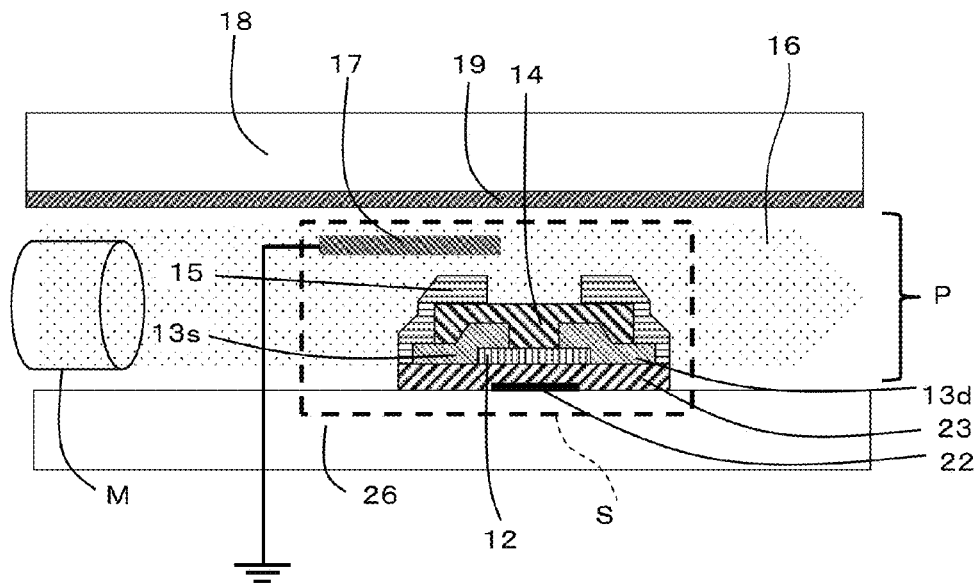
FIGS. 10A and 10B are cross-sectional views illustrating a TFT biosensor of sixth embodiment.
Figure 10B:
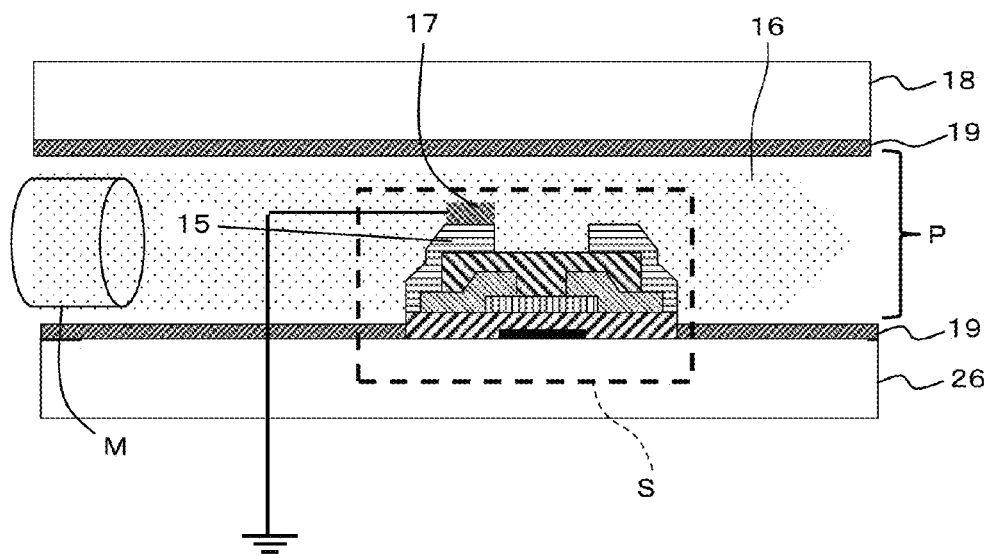
Figure 11:
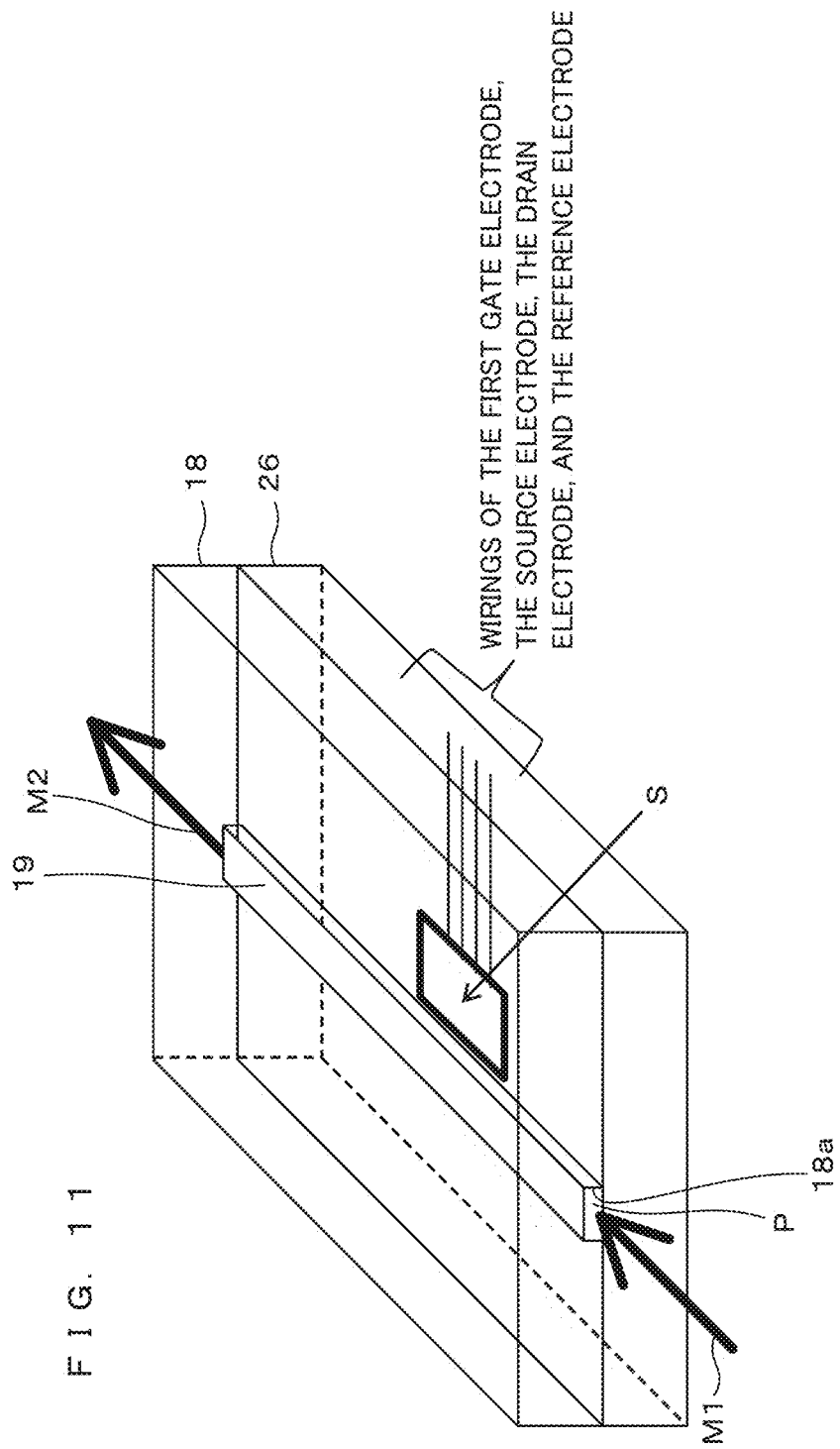
FIG. 11 is a schematic view illustrating the TFT biosensor of the sixth embodiment.

A sixth embodiment is described using FIGS. 10A and 10B, and FIG. 11. FIGS. 10A and 10B are cross-sectional views illustrating a TFT biosensor of the sixth embodiment, and FIG. 11 is a schematic view thereof.

As illustrated in FIG. 10A, in the TFT biosensor of the sixth embodiment, a thin film transistor, which includes the first gate electrode 22, the first gate insulating film 23, the semiconductor active layer 12, the source electrode 13s and drain electrode 13d, the ion-sensitive insulating film 14, and the protective insulating film 15, is formed on a first insulating substrate 26. In addition, in the TFT biosensor of the sixth embodiment, the reference electrode 17 is disposed at the spatially separated position from the ion-sensitive insulating film 14. In an example illustrated in FIG. 10A, the reference electrode 17 is disposed at the spatially separated position from the protective insulating film 15, but there is no limitation to the disposition. As illustrated in FIG. 10B, the reference electrode 17 may be formed on the protective insulating film 15. In this case, a silver thin film is formed on the protective insulating film 15, and is immersed in hydrochloric acid and the like to form a silver chloride film on a surface of the silver thin film. Then, a stacked thin film of silver chloride/silver is patterned to a desired shape to form the reference electrode 17. A configuration, which includes the thin film transistor and the reference electrode 17, is referred to as a thin film transistor sensor unit S. An example of the thin film transistor sensor unit S is the TFT biosensor 101 in FIG. 1, the TFT biosensor 201 in FIGS. 3 and 4, and the TFT biosensor 301 in FIG. 5.

In addition, in the sixth embodiment, the enzyme 19 having substrate-specificity for the biological material is formed on the second insulating substrate 18. The enzyme 19 may be formed on the entirety of the second insulating substrate 18. In addition, a groove may be formed in the second insulating substrate 18 in advance, and the enzyme 19 may be selectively formed at the groove portion. In a case where the enzyme 19 is formed on the entirety of the second insulating substrate 18, the first insulating substrate 26 and the second insulating substrate 18 are fixed in a state in which the ion-sensitive insulating film 14 and the enzyme 19 face each other and a space is secured therebetween. This space becomes a flow path P through which the solution that includes the sensing object material 16 flows.

In addition, the configuration, in which the groove is formed in the second insulating substrate 18, is illustrated in FIG. 11. In an example illustrated in FIG. 11, the groove 18a having a predetermined width is formed at an appropriate site in one surface of the second insulating substrate 18 (in FIG. 11, the central portion of a lower surface in a horizontal direction), and the enzyme 19 is formed on an inner side of groove 18a. In a case where the groove 18a is formed in the second insulating substrate 18, it is possible to closely join the first insulating substrate 26 and the second insulating substrate 18. When the two insulating substrates 26 and 18 are joined, a space is formed due to the groove 18a, and this space becomes the flow path P through which the solution that includes the sensing object material 16 flows. It is necessary for the insulating substrates 18 and 26 to be joined in a state in which the groove 18a and the thin film transistor sensor unit S two-dimensionally overlap each other.

Further, in the TFT biosensor of the sixth embodiment, a mechanism (for example, a pump) M, which supplies the solution that includes the sensing object material 16 to the flow path P and controls the flow of the sensing object material 16, may be provided regardless of whether or not the groove 18a exists. For example, as illustrated in FIG. 11, the sensing object material 16 is supplied by the mechanism M from one end side of the flow path P as indicated by an arrow M1. The sensing object material 16 passes through a portion on the thin film transistor sensor unit S in the flow path P, and is discharged from the other end side of the flow path P as indicated by an arrow M2. Even in the example illustrated in FIGS. 10A and 10B, for example, the sensing object material 16 may be allowed to pass through the flow path P by the mechanism M from a left side of the thin film transistor sensor unit S to a right side thereof.

FIG. 10B illustrates a case where the enzyme 19 is also formed on the first insulating substrate 26. As is the case with the above description, the thin film transistor is formed on the first insulating substrate 26, and then the enzyme 19 is formed in a desired region other than the thin film transistor region. Although not illustrated in the drawing, it is also possible to employ a configuration in which the enzyme 19 is formed only in a region other than the thin film transistor region on the first insulating substrate 26, and the enzyme 19 is not formed on the second insulating substrate 18.

In the sixth embodiment, the enzyme 19 is formed on the second insulating substrate 18, or the region on the first insulating substrate 26 other than the thin film transistor region, that is, on a wide area at the spatially separated position from the pH sensing unit (thin film transistor sensor unit S). Accordingly, two functions including a function of the pH sensing unit and biomolecule recognition function do not inhibit each other. In addition, it is possible to increase the amount of enzyme per unit area in the pH sensing unit, and thus it is possible to enlarge the amount of pH variation due to enzyme reaction. As a result, it is possible to raise detection sensitivity for the biological material.

Furthermore, although not illustrated in FIGS. 10A and 10B, and FIG. 11, as illustrated in FIG. 1, the TFT biosensor of the sixth embodiment includes any one of the voltage detection unit 20 that reads out the potential difference between the source electrode 13s and the gate electrode 22, and the current detection unit 21 that reads out the current that flows to the source electrode 13s or the drain electrode 13d.

(Example 8)

Example 8 of the sixth embodiment is described using FIG. 10A.

In the TFT biosensor of Example 8, an aluminum alloy film is formed on a glass substrate that is the first insulating substrate 26 by sputtering method, and is patterned in a desired shape in order to form the first gate electrode 22. Then, the silicon oxide film having the film thickness of 200 nm is formed by plasma CVD method as the first gate insulating film 23.

In addition, the In—Ga—Zn—O film is formed as the semiconductor active layer 12 by sputtering method, and is patterned in a desired shape. After performing annealing in the air at 400° C. for one hour, the molybdenum film is formed by sputtering method, and is patterned in a desired shape to form the source electrode 13s and the drain electrode 13d. Continuously, the tantalum oxide film having the film thickness of 100 nm is formed as the ion-sensitive insulating film 14 by sputtering method, and is patterned in a desired shape.

In addition, the annealing process is performed in the air at 300° C. for one hour, and the protective insulating film 15 is formed in the desired shape by using silicone resin. When considering that a specific dielectric constant of silicon oxide is 4, and a specific dielectric constant of tantalum oxide is 20, in this configuration, the electrostatic capacity per unit area of the ion-sensitive insulating film 14 is approximately 10 times larger than the electrostatic capacity per unit area of the first gate insulating film 23. According to this, it is possible to realize pH detection sensitivity of approximately 10 times larger than the theoretical limit of the Nernst theory.

Next, the manufacturing apparatus fixes glucose oxidase as the enzyme 19 onto the glass substrate that is the second insulating substrate 18. Specifically, a reagent, which is obtained by dissolving 10% glucose oxidase, 10% bovine serum albumin, and 8% glutaraldehyde in a phosphate buffer, is prepared, and is used as the enzyme 19. The manufacturing apparatus applies the enzyme 19 onto the glass substrate, patterns the enzyme 19 to a desired shape, and dries the enzyme 19 at room temperature for 20 minutes, thereby fixing the enzyme 19 onto the second insulating substrate 18.

The manufacturing apparatus sets the two sheets of glass substrates (insulating substrates 26 and 18), which are manufactured as described above, to face each other so that the tantalum oxide film (ion-sensitive insulating film 14) and the glucose oxidase (enzyme 19) face each other, and seals peripheral edge portions of the two sheets of glass substrates 26 and 18 in a state in which a gap of several mm from several 100 μm to is opened as the flow path P. In addition, the reference electrode 17, which is formed from silver/silver chloride, is inserted into the gap. As a mechanism M that introduces a test liquid (solution that includes the sensing object material 16) into the gap (flow path P), for example, a micropump is provided.

As the test liquid, a glucose aqueous solution, which has various concentrations, is introduced into the gap (flow path P) by using the micropump, and a minute variation in a proton concentration, which is caused by new generation of protons through the enzyme reaction between glucose and glucose oxidase (enzyme 19), is detected from the pH variation of the test liquid. In this example, the glucose oxidase that is the enzyme 19 is fixed to a wide region on the surface of the glass substrate (second insulating substrate 18), and thus an area, in which the glucose oxidase comes into contact with the glucose aqueous solution that is the test liquid, is sufficiently great. Accordingly, the enzyme reaction efficiently progresses, and a variation in a glucose concentration of approximately 0.001 mM can be detected in combination with high sensitivity in pH sensing by using a top gate effect.

(Example 9)

Example 9 of the sixth embodiment is described using FIG. 11. As is the case with Example 8 as described above, a manufacturing apparatus in Example 9 forms the thin film transistor sensor unit S on the glass substrate that is the first insulating substrate 26. Wirings of the first gate electrode 22, the source electrode 13s, the drain electrode 13d, and the reference electrode 17 of the thin film transistor sensor unit S are lead out to the outside of the glass substrate so as to apply an operation electrical signal from the outside. In addition, the manufacturing apparatus forms the groove 18a in the glass substrate that is the second insulating substrate 18. For example, the glass is etched with fluoric acid to form the groove 18a having a width of 2 mm and a depth of 800 μm.

Then, as is the case with Example 8, the manufacturing apparatus fixes the glucose oxidase (enzyme 19) to the concave surface (inner surface) of the groove 18a. In addition, the manufacturing apparatus joins two sheets of glass substrates (insulating substrate 26 and 18) in an arrangement in which the thin film transistor sensor unit S and the groove 18a two-dimensionally overlap each other. That is, in a state in which the thin film transistor sensor unit S is covered with the groove 18a, the two insulating substrates 26 and 18 are joined to each other.

With respect to this device, as the test liquid, a glucose solution, which has various concentrations, is introduced into the flow path P from one side of the flow path P formed by the groove 18a by using the micropump M, and the test liquid is discharged from the other side of the flow path P. When the test liquid flows at the inside of the flow path P, the test liquid reacts with the enzyme 19 that is fixed at the inside of the flow path P, thereby generating protons. It is possible to detect a minute glucose concentration by detecting a generation amount of protons as the variation in the electric double-layer potential, by using the thin film transistor sensor unit S. With regard to the structure of the flow path P, it is possible to employ a structure, in which a wide-width region is partially configured partway through the flow path P to increase an area capable of fixing the enzyme 19, without limitation to a linear structure as illustrated in FIG. 11.

(Seventh Embodiment)

Figure 12A:
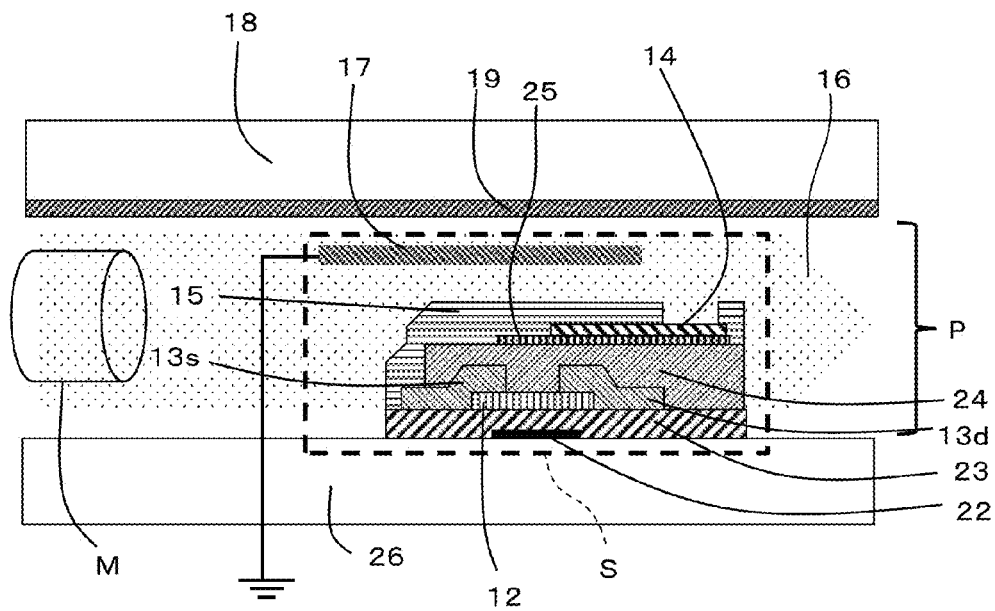
FIGS. 12A and 12B are cross-sectional views illustrating a TFT biosensor of seventh embodiment.
Figure 12B:
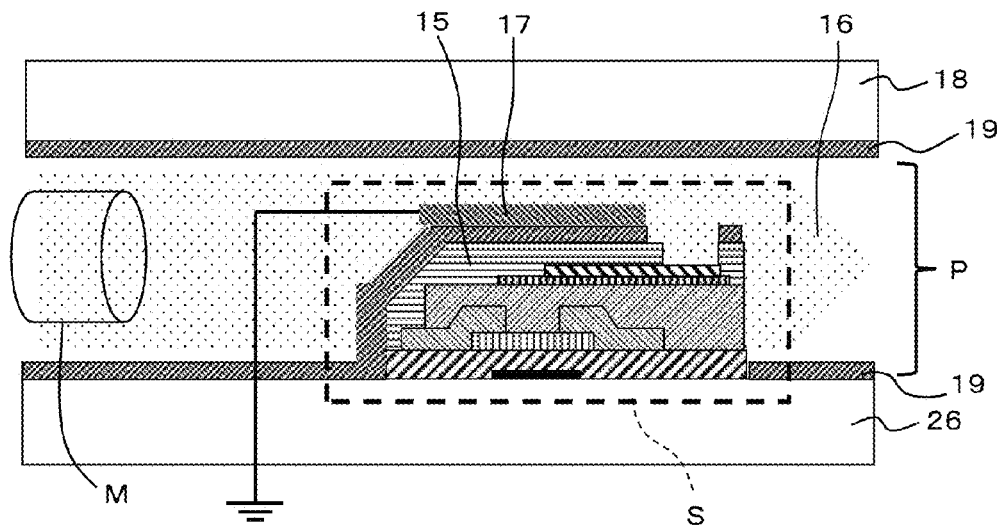

The description will be given of seventh embodiment with reference to FIGS. 12A and 12B. FIGS. 12A and 12B are cross-sectional views illustrating a TFT biosensor of the seventh embodiment. As illustrated in FIG. 12A, in the TFT biosensor of the seventh embodiment, the thin film transistor, which includes the first gate electrode 22, the first gate insulating film 23, the semiconductor active layer 12, the source electrode 13s and drain electrode 13d, the second gate insulating film 24, the second gate electrode 25, the ion-sensitive insulating film 14, and the protective insulating film 15, is formed on the first insulating substrate 26. The second gate electrode 25 has a shape that extends from a position, which faces the first gate electrode 22, in a horizontal direction, and the ion-sensitive insulating film 14 is formed over the extension region. An opening is formed in a part of a region, which extends in the horizontal direction, on the ion-sensitive insulating film 14, and the protective insulating film 15 is formed in a region other than the opening. That is, the channel portion and ion-sensitive portion of the thin film transistor are disposed at positions which two-dimensionally deviate from each other. This configuration is different from the configuration of FIGS. 10A, 10B, and 11 in which the channel portion and the ion-sensitive portion are disposed at positions which two-dimensionally overlap each other.

In addition, in the TFT biosensor of the seventh embodiment, the reference electrode 17 is disposed at the spatially separated position from the ion-sensitive insulating film 14. In FIG. 12A, the reference electrode 17 is disposed at the spatially separated position from the protective insulating film 15, but the reference electrode 17 may be formed on the protective insulating film 15 as illustrated in FIG. 12B without limitation to the above-described disposition. In this case, a silver thin film is formed on the protective insulating film 15, and is immersed in hydrochloric acid and the like to form a silver chloride film on a surface of the silver thin film. Then, a stacked thin film of silver chloride/silver is patterned to a desired shape to form the reference electrode 17. In this example, the configuration including the thin film transistor and the reference electrode 17 is also referred to as the thin film transistor sensor unit S. An example of the thin film transistor sensor unit S is the TFT biosensor 401 in FIG. 6, the TFT biosensor 501 in FIG. 7, the TFT biosensor 601 in FIG. 8, and the TFT biosensor 701 in FIG. 9.

In addition, in the seventh embodiment, the enzyme 19 having substrate-specificity for the biological material is formed on the second insulating substrate 18. The enzyme 19 may be formed on the entirety of the second insulating substrate 18. In addition, after forming the groove 18a in the second insulating substrate 18 in advance similar to FIG. 11, the enzyme 19 may be selectively formed in the portion of the groove 18a. The first and second insulating substrates 26 and 18 are fixed in a state in which the ion-sensitive insulating film 14 and the enzyme 19 face each other, and the space is secured therebetween. The space becomes the flow path P through which the sensing object material 16 flows. In addition, in the case of forming the groove 18a in the second insulating substrate 18, it is possible to closely join the first and second insulating substrates 26 and 18. In this case, it is necessary to perform the joining so that the groove 18a and the thin film transistor sensor unit S two-dimensionally overlap each other. Further, the mechanism (for example, a pump and the like) M, which supplies the sensing object material 16 to the flow path P and controls the flow of the sensing object material 16, may be provided regardless of whether or not the groove 18a exists.

FIG. 12B illustrates a case where the enzyme 19 is also formed on the first insulating substrate 26. As described above, after forming the thin film transistor on the first insulating substrate 26, the enzyme 19 is formed in a desired region other than the thin film transistor region. Although not illustrated in the drawing, it is also possible to employ a configuration in which the enzyme 19 is formed only in a region other than the thin film transistor region on the first insulating substrate 26, and the enzyme is not formed on the second insulating substrate 18.

In the seventh embodiment, the enzyme 19 is formed on the second insulating substrate 18, or a region on the first insulating substrate 26 other than the thin film transistor region, that is, on a wide area at the spatially separated position from the pH sensing unit (thin film transistor sensor unit S). Accordingly, two functions including function of the pH sensing unit and biomolecule recognition function do not inhibit each other. In addition, it is possible to increase the amount of enzyme per unit area of the pH sensing unit, and thus it is possible to enlarge the variation amount of pH due to enzyme reaction. As a result, it is possible to raise detection sensitivity for the biological material. In addition, compared with the sixth embodiment, in the seventh embodiment, the ion-sensitive insulating film 14 exists at the position that is spaced away from the thin film transistor region. The ion-sensitive insulating film 14 is a portion with which a test liquid comes into contact, and in this example in which the portion is spaced away from the thin film transistor region, a probability that the test liquid penetrates into the thin film transistor sensor unit S decreases, and thus it is possible to expect long lifetime of the sensor element.

In addition, FIGS. 12A and 12B illustrate a configuration in which the ion-sensitive insulating film 14 is provided on the second gate electrode 25. However, in a case where the second gate electrode 25 itself has ion sensitiveness, the ion-sensitive insulating film 14 may not be provided.

(Example 10)

Example 10 of the seventh embodiment is described using FIG. 12A.

In the TFT biosensor of Example 10, the aluminum alloy film is formed on the glass substrate that is the first insulating substrate 26 by sputtering method, and is patterned in the desired shape in order to form the first gate electrode 22. Then, the silicon oxide film having the film thickness of 200 nm is formed as the first gate insulating film 23 by plasma CVD method.

In addition, the In—Ga—Zn—O film is formed as the semiconductor active layer 12 by sputtering method, and is patterned in the desired shape. After performing annealing in the air at 400° C. for one hour, the molybdenum alloy film is formed by sputtering method, and is patterned in the desired shape to form the source electrode 13s and the drain electrode 13d. Continuously, the tantalum oxide film having the film thickness of 100 nm is formed as the second gate insulating film 24 by sputtering method, and is patterned in the desired shape.

Next, after performing annealing in the air at 300° C. for one hour, the aluminum alloy film is formed as the second gate electrode 25, and is patterned in the desired shape. At this time, the second gate electrode 25 is set to have a shape that extends from the position that faces the first gate electrode 22 in a horizontal direction. In addition, the tantalum oxide film having the film thickness of 10 nm is formed as the ion-sensitive insulating film 14 on the second gate electrode 25, and is patterned in the desired shape.

Continuously, the protective insulating film 15 is formed in a desired shape by using epoxy resin. At this time, patterning is performed so that an opening is formed in a part of a region, which extends in the horizontal direction, on the ion-sensitive insulating film 14. When considering that the specific dielectric constant of the silicon oxide is 4, and the specific dielectric constant of the tantalum oxide is 20, in this configuration, the electrostatic capacity per unit area of the ion-sensitive insulating film 14 is approximately nine times larger than the electrostatic capacity per unit area of the first gate insulating film 23. According to this, it is possible to realize pH detection sensitivity of approximately nine times larger than the theoretical limit of the Nernst theory. The reason why the sensitivity slightly decreases compared with the case of Example 8 is as follows. In this example, it is necessary consider series connection between the tantalum oxide (second gate insulating film 24) having the film thickness of 100 nm and the tantalum oxide (ion-sensitive insulating film 14) having the film thickness of 10 nm as a capacity.

Next, the manufacturing apparatus fixes penicillinase as the enzyme 19 onto the glass substrate that is the second insulating substrate 18. For example, after preparing a reagent in which penicillinase is dissolved in a buffer solution, the manufacturing apparatus applies the reagent onto the glass substrate (second insulating substrate 18), and patterns the reagent to a desired shape. Then, the manufacturing apparatus dries the reagent at room temperature for 120 minutes to fix the enzyme 19 onto the second insulating substrate 18.

The manufacturing apparatus sets the two sheets of glass substrates to face each other so that the tantalum oxide film (ion-sensitive insulating film 14) and the penicillinase (enzyme 19) face each other, and seals the peripheral edge portion of the two sheets of glass substrates in a state in which a gap of several mm from several 100 μm is opened as the flow path P. In addition, the manufacturing apparatus inserts the reference electrode 17, which is formed from silver/silver chloride, into the gap. In addition, the manufacturing apparatus provides the micropump as the mechanism M that introduces a test liquid (solution that includes the sensing object material 16) into the gap (flow path P).

In the TFT biosensor that is manufactured as described above, as the test liquid, a penicillin aqueous solution, which has various concentrations, is introduced into the gap (flow path P) by using the micropump M, and a minute variation in a proton concentration, which is caused by new generation of protons through the enzyme reaction between penicillin and penicillinase (enzyme 19), is detected from the pH variation of the test liquid. The penicillin is hydrolyzed through the enzyme reaction between penicillin and penicillinase, and thus penicilloic acid and protons are generated. Particularly, in biosensor field, detection of a minute penicillin concentration is important, and it is necessary to sense a minute variation in the proton concentration which occurs by the enzyme reaction. In this example, the penicillinase, which is the enzyme 19, is fixed in a wide region on the surface of the glass substrate (second insulating substrate 18), and thus an area, in which the penicillin aqueous solution that is a test liquid and the penicillinase come into contact with each other, is sufficiently great.

Accordingly, the enzyme reaction efficiently progresses, and a variation in the penicillin concentration of approximately 0.001 mM can be detected in combination with high sensitivity in pH sensing by using a top gate effect. In addition, compared with the case of Example 8, in this example, the ion-sensitive unit exists at the position that is spaced from the thin film transistor region, and thus a probability that the penicillin aqueous solution, which is the test liquid, penetrates into the thin film transistor unit decreases. As a result, it is possible to realize long lifetime and a high yield ratio of the sensor element.

In Examples 1 to 7 as described above, the descriptions have been given of a case where a silicon wafer equipped with the thermal oxide film 10 is used, and as constituent elements of the thin film transistor, the silicon substrate 11 is allowed to operate as the gate electrode, and the thermal oxide film 10 is allowed to operate as the gate insulating film. However, there is no limitation thereto, and even in Examples 1 to 7, as is the case with Examples 8 to 10, the gate electrode may be formed with the metal on the glass substrate (first insulating substrate 26), and the gate insulating film (for example, a silicon oxide film, and the like) may be formed on the gate electrode by plasma CVD method or sputtering method. In addition, even in the case of Examples 1 to 7, the groove 18a may be formed in the second insulating substrate 18 similar to FIG. 11, and the enzyme 19a may be provided in the groove 18a.

In addition, in Examples 8 to 10, the enzyme 19 is fixed to the substrate (second insulating substrate 18) that is different from the substrate on the TFT sensor unit S side. Therefore, when the enzyme 19 is inactivated, it is possible to recover the sensor function by replacing only the enzyme substrate with new one while keeping the configuration other than the enzyme substrate (second insulating substrate 18). Accordingly, it is possible to provide the sensor having long lifetime with the small burden on a user. In addition, the function capable of replacing the enzyme substrate with new one represents that substitution with another enzyme is possible. That is, when considering the examples, for example, in a case where the substrate for glucose sensing and the substrate for penicillin sensing are provided as the enzyme substrate, it is possible to provide the TFT biosensor capable of realizing multi-item measurement by using the same TFT sensor substrate (first insulating substrate 26).

In addition, in the above-described examples, the descriptions have been given of a case where the first insulating substrate 26 and the second insulating substrate 18 are disposed to face each other or are joined to each other. However, there is no limitation thereto, and for example, the first insulating substrate 26, on which the thin film transistor sensor unit S is formed, may have a flat shape, and the second insulating substrate 18, to which the enzyme 19 is fixed, may have a cylindrical shape. In this case, the effect can be realized by a configuration in which the enzyme 19 is fixed to an inner side of the cylinder, and the first insulating substrate 26 is disposed in the cylinder. In this manner, the disposition of the first insulating substrate 26 and second insulating substrate 18 may be set in an arbitrary manner.

In addition, in the above-described examples, illustration has been given of a case where the concentration (pH) of hydrogen ions varies due to the enzyme reaction, and the concentration of biomaterial is sensed by detecting the pH variation. However, it is also possible to sense a concentration of an arbitrary ion that is generated in the enzyme reaction without limitation to the concentration of hydrogen ions. For example, in the case of performing sensing of the test liquid in which a cation such as Na ion and K ion is generated through enzyme reaction, the following thin film is used (also referred to "applied") as the ion-sensitive insulating film 14. This thin film is a thin film that is formed by mixing a compound including polypeptide such as valinomycin or crown ether that becomes a ligand as a basic skeleton, and a resin material, and by applying and baking the resultant mixed material. In this case, the ion-sensitive film also operates as enzyme. Even in the case of an anion without limitation to the cation, it is possible to use a ligand that is appropriate to the anion.

In addition, in the above-described examples, illustrated has been given of the case of using the oxide semiconductor as the semiconductor active layer 12. However, there is no limitation thereto, and it is also possible to use the following material (also referred to as a material quality) as the semiconductor active layer 12. Examples of the material include a silicon semiconductor such as amorphous silicon and polycrystalline silicon, a low-molecular-weight-based organic semiconductor (for example, pentacene and the like) that is capable of being formed as a film through deposition, a high-molecular-weight-based organic semiconductor that is capable of being formed as a film through application, and a carbon material such as carbon nanotube and graphene. As a specific example, FIG. 13 illustrates a configuration in which an organic semiconductor is used as the active layer.

Figure 13:
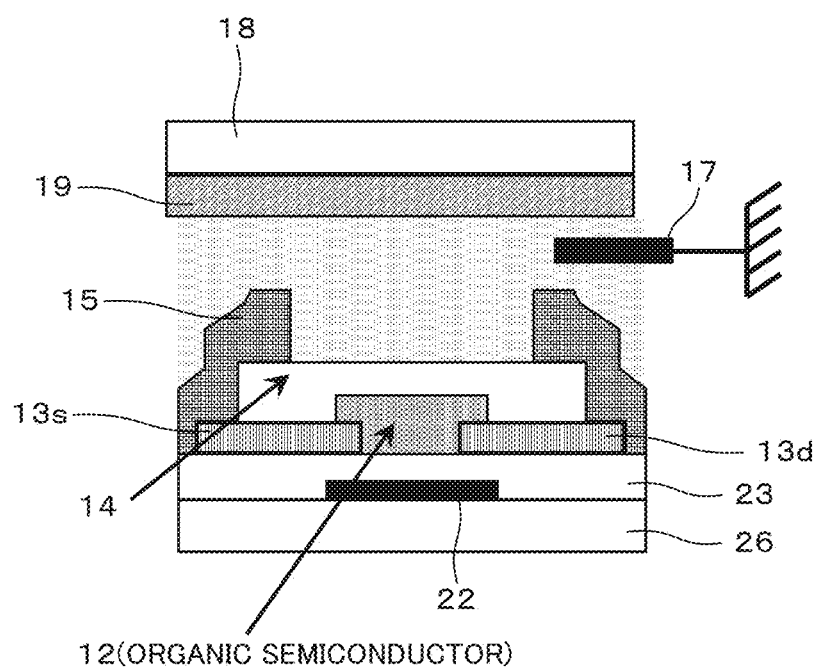
FIG. 13 is a cross-sectional view illustrating a TFT biosensor in which an organic semiconductor is used as a semiconductor active layer.

FIG. 13 is a cross-sectional view illustrating a TFT biosensor in which an organic semiconductor is used as the semiconductor active layer 12. The TFT biosensor illustrated in FIG. 13 has the same configuration as the TFT biosensor of Example 8 illustrated in FIG. 10A except that the semiconductor active layer 12 is constituted by the organic semiconductor. The oxide semiconductor frequently appears only n-type conduction, and the organic semiconductor frequently appears only p-type conduction.

This kind of single polarity is easy to realize a top gate effect, and is easy to realize high sensitivity in accordance with a capacity ratio.

(Eighth Embodiment)

Figure 14:
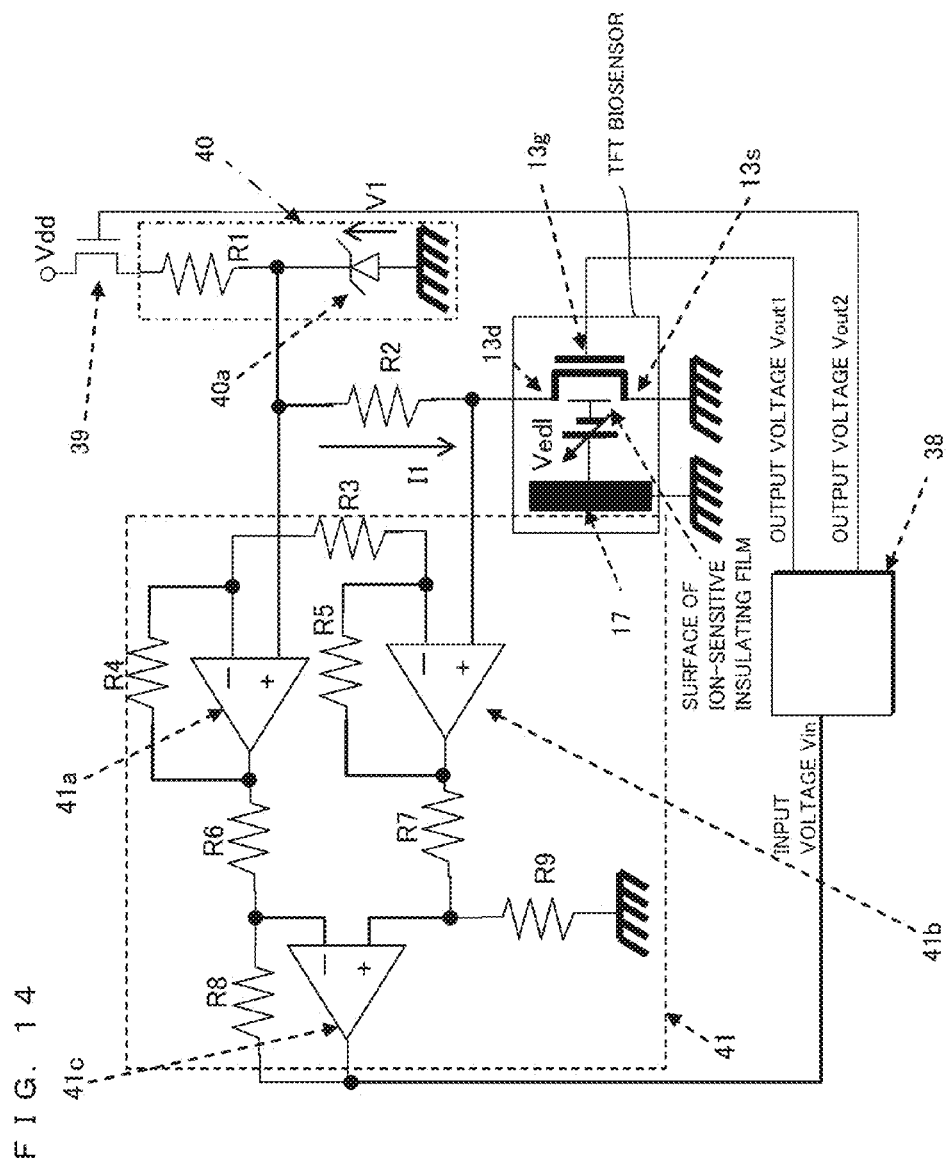
FIG. 14 is a circuit diagram of a TFT biosensor device of eighth embodiment.

FIG. 14 is a circuit diagram of a TFT biosensor device of eighth embodiment. FIG. 15 is a view illustrating a configuration example of a microprocessor 38 in the TFT biosensor device in FIG. 14. The TFT biosensor device (detection device) of the eighth embodiment includes any one of the TFT biosensors 101 to 701 of Examples 1 to 10 described above. The TFT biosensor in FIG. 14 is any one of the TFT biosensors 101 to 701.

In addition, the TFT biosensor device includes a microprocessor (processor) 38, a constant voltage circuit (voltage application circuit) 40, and a current-voltage conversion circuit (detection circuit) 41. The constant voltage circuit 40 applies a voltage (first voltage) between the source electrode 13s and drain electrode 13d of the TFT biosensor. The current-voltage conversion circuit 41 detects a current, which flows between the source electrode 13s and drain electrode 13d, as a voltage (second voltage). The microprocessor 38 controls a potential of the gate electrode 13g of the TFT biosensor and the constant voltage circuit 40 based on the voltage that is detected by the current-voltage conversion circuit 41.

The constant voltage circuit 40 includes a Zener diode 40a and a resistor R1. The Zener diode 40a is connected to a transistor 39 through the resistor R1. The resistor R1 is connected to a power supply Vdd through the transistor 39. An output terminal of the constant voltage circuit 40 is connected to the drain electrode 13d of the TFT biosensor through a resistor R2. In a case where the transistor 39 is turned on by the microprocessor 38, the constant voltage circuit 40 applies a reverse breakdown voltage (V1) of the Zener diode 40a between the source electrode 13s and the drain electrode 13d of the TFT biosensor through the resistor R2.

The current-voltage conversion circuit 41 converts a minute current between the source electrode 13s and the drain electrode 13d into a voltage value. The current-voltage conversion circuit 41 includes a first operational amplifier 41a, a second operation amplifier 41b, and a third operational amplifier 41c.

Specifically, the current-voltage conversion circuit 41 includes the three operational amplifiers 41a to 41c, and seven resistors R3 to R9. A positive input terminal (hereinafter, referred to as "+input terminal") of the first operational amplifier 41a is connected to an output terminal of the constant voltage circuit 40, and a +input terminal of the second operation amplifier 41b is connected to the drain electrode 13d of the TFT biosensor. In addition, an output terminal and a negative input terminal (hereinafter, referred to as "—input terminal") of the first operational amplifier 41a are connected to each other through the resistor R4, and an output terminal and a —input terminal of the second operation amplifier 41b are connected to each other through the resistor R5. I addition, the —input terminal of the first operational amplifier 41a and the —input terminal of the second operation amplifier 41b are connected to each other through the resistor R3. A —input terminal of the third operational amplifier 41c is connected to the output terminal of the first operational amplifier 41a through the resistor R6, and a +input terminal of the third operational amplifier 41c is connected to the output terminal of the second operation amplifier 41b through the resistor R7. In addition, the +input terminal of the third operational amplifier 41c is connected to a ground through the resistor R9, and an output terminal and the —input terminal of the third operational amplifier 41c are connected to each other through the resistor R8. In addition, an output terminal of the third operational amplifier 41c becomes an output terminal of the current-voltage conversion circuit 41. The current-voltage conversion circuit 41 outputs a voltage value (input voltage Vin), which is obtained by converting a minute current between the source electrode 13s and the drain electrode 13d, to the microprocessor 38.

As illustrated in FIG. 15, the microprocessor 38 includes an operation unit 38a and a storage unit 38b. For example, the operation unit 38a is constituted by one or a plurality of central processing units (CPUs), a multi-core CPU, and the like. For example, the storage unit 38b includes a random access memory (RAM) 38ba, a read only memory (ROM) 38bb, and the like. The operation unit 38a reads out a control program, which is stored in the ROM 38bb into the RAM 38ba, and executes the control program so as to perform various operation processes. For example, when activating the microprocessor 38, the operation unit 38a reads out a control program file (execution file) for execution of a first operation process from the ROM 38bb, and develops and executes the control program file in the RAM 38ba, thereby functioning as a program module of a first operation unit 38aa. In addition, the operation unit 38a reads out a control program file for execution of a second operation process from the ROM 38bb, and develops and executes the control program file in the RAM 38ba, thereby functioning as a program module of a second operation unit 38ab.

The ROM 38bb is a non-volatile memory, and stores a control program for execution of a predetermined operation process by the operation unit 38a, and a control variable that is used when the operation unit 38a performs a predetermined operation process, various pieces of data, a table, and the like in advance. For example, in the case of allowing the operation unit 38a to perform an operation related to a proportional-integral-differential (PID) control, a control program for realization of the PID control and a control variable that is used in the PID control are stored in the ROM 38bb. In addition, in the case of allowing the operation unit 38a to perform an operation related to a proportional-integral (PI) control, a control program for realization of the PI control and a control variable that is used in the PI control are stored in the ROM 38bb. In addition, in the case of allowing the operation unit 38a to perform an operation related to a proportional (P) control, a control program for realization of the P control and a control variable that is used in the P control are stored in the ROM 38bb. The RAM 38ba is a rewritable memory, and temporarily stores data that is generated during an operation process by the operation unit 38a.

The microprocessor 38 acquires the voltage value, which is output from the current-voltage conversion circuit 41, as an input voltage Vin. The operation unit 38a (first operation unit 38*aa*) performs a predetermined operation (for example, the PID control, the PI control, and the P control) based on the input voltage Vin that is acquired from the current-voltage conversion circuit 41 and the control variable that is stored in the ROM 38*bb* to calculate the voltage value that is applied to the gate electrode 13*g* of the TFT biosensor. Furthermore, the first operation unit 38*aa* calculates a voltage value (output voltage Vout1 that is applied to the gate electrode 13*g*) so that the voltage that is applied between the source electrode 13*s* and the drain electrode 13*d* by the constant voltage circuit 40, and the voltage between the source electrode 13*s* and the drain electrode 13*d*, which is detected by the current-voltage conversion circuit 41, become constant. The operation unit 38*a* controls a voltage that is applied to the gate electrode 13*g* of the TFT biosensor based on the voltage value (output voltage Vout1) that is calculated. Specifically, the microprocessor 38 applies the output voltage Vout1 of the voltage value, which is calculated by the operation unit 38*a*, to the gate electrode 13*g*. In addition, the operation unit 38*a* (second operation unit 38*ab*) calculates an ion concentration, which corresponds to the output voltage Vout1, based on the voltage value (output voltage Vout1) that is calculated, and the table that is stored in the ROM 38*bb*. Specifically, the second operation unit 38*ab* reads out the ion concentration, which corresponds to the output voltage Vout1, from the table.

In addition, the operation unit 38*a* applies a voltage (output voltage Vout2) for turning ON or OFF of the transistor 39 to the transistor 39.

In the TFT biosensor device having the above-described configuration, in the case of performing sensing by the TFT biosensor, the microprocessor 38 sets the potential of the source electrode 13*s* and the potential of the reference electrode 17 to the same potential, and controls the potential between the silicon substrate 11 that becomes the gate electrode 13*g* and the source electrode 13*s* so that a predetermined current I1 flows between the source electrode 13*s* and the drain electrode 13*d*.

In the example illustrated in FIGS. 14 and 15, the microprocessor 38 switches the potential of the source electrode 13*s* to the source potential or the reference potential and allows the potential of the silicon substrate 11 that becomes the gate electrode 13*g* to vary. The microprocessor 38 reads out potential difference, which is caused by the ion concentration in the sensing object material 16, between the gate electrode 13*g* and the source electrode 13*s*. In addition, a table (correspondence table), in which a correspondence between the ion concentration and the potential difference (voltage value) between the gate electrode 13*g* and the source electrode 13*s* is stored as a characteristics of the TFT biosensor, is stored in the storage unit 38*b* (ROM 38*bb*) in advance. The ion concentration, which corresponds to the read-out potential difference between the gate electrode 13*g* and the source electrode 13*s*, in the sensing object material 16 is sensed (specified) with reference to the table.

The current-voltage conversion circuit 41 converts a minute current between the source electrode 13*s* and drain electrode 13*d* into a voltage value, and applies the voltage value, which is converted, to the microprocessor 38 as the input voltage Vin. The microprocessor 38 controls the voltage (output voltage Vout1), which is applied to the gate electrode 13*g* (silicon substrate 11) of the TFT biosensor so that the input voltage Vin becomes a constant value. The current-voltage conversion circuit 41 converts the drain-to-source current (Ids) of the TFT that depends on ion concentration in the object material into the voltage signal. The microprocessor 38 acquires the voltage signal from the current-voltage conversion circuit 41 and outputs a voltage signal (Vg-s) to the gate electrode 13*g* of the TFT so that the predetermined current (Ids) flows between the drain electrode 13*d* and source electrode 13*s* regardless of ion concentration in the object material. In other words, the microprocessor 38 functions as a feedback circuit to keep the current (Ids) constant regardless of ion concentration in the object material, and thus the TFT biosensor (pH sensor) operates in a constant-voltage (Vg-s) and constant-current (Ids) mode. In the case of stopping the operation of the TFT biosensor, the microprocessor 38 does not output the output voltage Vout1, and in the case of operating the TFT biosensor, the microprocessor 38 outputs the output voltage Vout1.

In the eighth embodiment, the operation unit 38*a* executes a control program that is stored in the storage unit 38*b* (ROM 38*bb*) to realize a process in the microprocessor 38. In addition to this, a part or the entirety of the process, which is executed by the operation unit 38*a*, may be realized by a dedicated hardware circuit.

(Example 11)

Example 11 of the eighth embodiment is described using FIGS. 14 and 15. Characteristics of the TFT biosensor temporally vary, and thus the microprocessor 38 performs the following process. Specifically, when sensing an ion concentration, the microprocessor 38 sets the potential of the source electrode 13*s*, and each potential of the drain electrode 13*d* and the gate electrode 13*g* (silicon substrate 11) to the same potential. Then, the microprocessor 38 applies a predetermined potential to the drain electrode 13*d* and the gate electrode 13*g* (silicon substrate 11). In other words, in the TFT biosensor, the potential difference between the source electrode 13*s* and the drain electrode 13*d* is controlled by using the constant voltage circuit 40, the microprocessor 38 that controls the constant voltage circuit 40, and the transistor 39.

Specifically, the microprocessor 38 controls the transistor 39 in accordance with the output voltage Vout2 to set the output potential (potential of the drain electrode 13*d*) of the constant voltage circuit 40 to the same potential as the potential of the source electrode 13*s*. In addition, the microprocessor 38 sets the potential of the silicon substrate 11, which becomes the gate electrode 13*g*, to the same potential as the potential of the source electrode 13*s* in accordance with the output voltage Vout1. Then, after passage of a predetermined time, the microprocessor 38 control the transistor 39 in accordance with the output voltage Vout2 to fix the potential difference between the source electrode 13*s* and the drain electrode 13*d* to the reverse breakdown voltage (V1) of the Zener diode 40*a*. In addition, the current-voltage conversion circuit 41 detects a minute current, which flows between the source electrode 13*s* and the drain electrode 13*d*, as a voltage value by removing an in-phase noise, and applies the voltage value (input voltage Vin), which is detected, to the microprocessor 38.

The microprocessor 38 controls the potential of the silicon substrate 11, which becomes the gate electrode 13*g*, through the PID control, for example, in accordance with a control variable obtained from characteristics illustrated in FIG. 16 so that the voltage value (input voltage Vin) acquired from the current-voltage conversion circuit 41 becomes the constant value. Furthermore, the control variable is stored in the storage unit 38*b* (ROM 38*bb*). The microprocessor 38 calculates the voltage value (output voltage Vout1), which is applied to the gate electrode 13*g* (silicon substrate 11) through the PID control based on the voltage value (input voltage Vin) that is acquired from the current-voltage conversion circuit 41, and the control variable that is stored in the storage unit 38*b*.

In addition, the microprocessor 38 applies the output voltage Vout1 to the gate electrode 13*g*. According to this, the microprocessor 38 sets the current value between the source electrode 13*s* and the drain electrode 13*d* to the predetermined value I1. When sensing that the current value between the source electrode 13*s* and the drain electrode 13*d* becomes the predetermined value I1, the microprocessor 38 calculates the ion concentration in accordance with the measurement method that uses the potential of the silicon substrate 11 that becomes the gate electrode 13*g*, and the characteristics illustrated in FIG. 16.

When the ion concentration is calculated, the microprocessor 38 sets the potential of the silicon substrate 11 that becomes the gate electrode 13*g* to the same potential as the potential of the source electrode 13*s* in accordance with the output voltage Vout1. In addition, the microprocessor 38 controls the transistor 39 in accordance with the output voltage Vout2, and sets the potential of the drain electrode 13*d* to the same potential as the potential of the source electrode 13*s*.

Hereinafter, the description will be given of the measurement method by the TFT biosensor device with the potential of the source electrode 13*s* of the TFT biosensor set as a reference.

FIG. 16 is an explanatory view of a measurement principle in the TFT biosensor device of the eighth embodiment. In FIG. 16, the horizontal axis represents the voltage (Vg-s) of the gate electrode 13*g* with the potential of the source electrode 13*s* set as a reference. In addition, the vertical axis represents the current that flows between the source electrode 13*s* and the drain electrode 13*d*. FIG. 16 schematically illustrates characteristics of the gate electrode voltage (Vg-s) to the source-drain current. Here, when sensing the ion concentration, the potential difference between the source electrode 13*s* and the drain electrode 13*d* is fixed to V1 (the reverse breakdown voltage of the Zener diode 40*a*) as described above.

When the ion concentration in the sensing object material 16 varies, and the electric double-layer potential difference (Ved1 in FIG. 14) at the interface between the sensing object material 16 and the ion-sensitive insulating film 14 varies to +0.1 V, 0 V, and −0.1 V, the microprocessor 38 controls the output voltage Vout1 with respect to the silicon substrate 11, which becomes the gate electrode 13*g*, to 0.5 V, 1 V, and 1.5 V so as to allows the current value I1, which is calculated in advance from the characteristics of the TFT biosensor, to flow. At this time, the microprocessor 38 calculates an operation amount of the output voltage Vout1 with the following Expression (1) so as to stabilize the control. In addition, the microprocessor 38 applies the output voltage Vout1, which is calculated, to the gate electrode 13*g* (silicon substrate 11).

Operation amount=*Kp*×(deviation)+*Ki*×(accumulated value of deviation)+*Kd*×(difference from immediately previous deviation) (1)

Furthermore, Kp, Ki, and Kd are control variables, and are, for example, 0.6, 0.7, and 0.3, respectively. The deviation is a difference between the value (input voltage Vin acquired from the current-voltage conversion circuit 41) that is obtained by reading out the current between the source electrode 13*s* and the drain electrode 13*d* as a voltage, and a predetermined value that is set in advance.

The output voltage Vout1 from the microprocessor 38 is the same as the voltage Vg-s of the gate electrode 13*g*. Accordingly, in various ion concentrations, reading-out of the output voltage Vout1 by the microprocessor 38 in order for the constant current I1 to flow is the same as reading-out that Vg-s varies in which manner in order for the constant current I1 to flow. This is none other than sensing of a shift amount in characteristics of the gate-source voltage to the drain-source current in various ion concentrations (as illustrated in FIG. 16). A table, in which the concentration of hydrogen ions and the gate electrode voltage Vg-s are associated using a discrete value as illustrated in FIG. 17, is stored in the storage unit 38*b* (ROM 38*bb*) in advance. Accordingly, the microprocessor 38 specifies the concentration of hydrogen ions from the output voltage Vout1, which is read out, by using the table.

FIG. 17 is a view illustrating a table in which a correspondence between the concentration of hydrogen ions and the gate electrode voltage Vg-s is stored. The table in FIG. 17 includes a first column in which the concentration [pH] of hydrogen ions is stored, a second column in which the voltage Vg-s [V] of the gate electrode is stored, and a third column in which the source-drain current I1 [nA] is stored. The table illustrated in FIG. 17 stores the concentration of hydrogen ions, the gate electrode voltage Vg-s, and the current between the source and drain electrodes in correspondence with each other. Furthermore, the voltage Vg-s, which is stored in the table, of the gate electrode 13*g* is a voltage so as to set the current, which flows between the source electrode 13*s* and the drain electrode 13*d*, to the constant current I1, and thus the column of the current between the source and drain electrodes may not be provided in the table.

As described above, when using the biosensor, which is constituted by using the thin film transistor described in the first to seventh embodiments, to the TFT biosensor unit S of the eighth embodiment, it is possible to realize the TFT biosensor device with higher sensitivity compared with the related art.

(Example 12)

As a modification example of the eighth embodiment, the description will be given of a measurement unit in consideration of a variation of the TFT biosensor with the passage of time. When observing the variation in the drain current of the TFT biosensor of the disclosure with the passage of time in the test liquid with constant pH under a constant gate voltage and a constant drain voltage, in an ideal state, a constant drain current is always obtained. However, in many cases, the drain current drifts to a direction in which the drain current decreases with the passage of time.

In an environment in which the drift of the drain current occurs, measurement with high stability is not realized. The drift is caused by slow progress of ion adsorption and ion migration at the interface of the ion-sensitive insulating film 14, and it can be said that the drift is a requisite variation for carrying out in-liquid measurement. As means for suppressing the drift, carrying-out of intermittent measurement is effective. During a measurement operation, when a voltage is not applied, or an idle period, in which a voltage lower than a voltage during measurement is applied, is provided, it is possible to suppress the drift during measurement, or it is possible to periodically initialize a sensor state while denying a variation due to the drift.

FIG. 18 is an explanatory view of a measurement method in the TFT biosensor device of Example 12. In FIG. 18, the horizontal axis represents time, and the vertical axis represents a current that flows between the source electrode 13*s* and the drain electrode 13*d*. FIG. 18 represents the variation in the drain current with passage of time in the TFT biosensor device of Example 12, and a result that is obtained by performing intermittent measurement by using the TFT biosensor. For example, a measurement period in which a predetermined voltage is applied to the gate electrode 13*g* and the drain electrode 13*d*, respectively, to measure a drain current, and an idle period in which a voltage that is applied to the gate electrode 13*g* and the drain electrode 13*d* is set to 0 V and measurement is not performed, are repeated for 120 seconds.

With regard to the TFT biosensor of Example 12, first, the semiconductor active layer 12 that is formed of In—Ga—Zn—O and has the thickness of 50 nm, the source electrode 13*s* and the drain electrode 13*d* which are formed of molybdenum metal and have the thickness of 100 nm, and the ion-sensitive insulating film 14 that is formed of tantalum oxide and has the thickness of 100 nm are formed on the silicon substrate 11 covered with the thermal oxide film 10 by sputtering method using metal mask. In addition, after performing annealing in the air at 350° C. for one hour, the protective insulating film 15 formed of silicone resin covers the ion-sensitive insulating film 14 except for a part thereof.

Next, the manufacturing apparatus immerses a thin film transistor in a McIlvaine buffer solution set to pH 6.0. The McIlvaine buffer solution is adjusted by 0.05 mM/L of a citric acid aqueous solution and 0.025 mM/L of a sodium hydrogen phosphate aqueous solution.

In the TFT biosensor having the above-described configuration, in the case of being intermittently operated in accordance with the control by the microprocessor 38, a measurement result illustrated in FIG. 18 is obtained. FIG. 18 illustrates the result obtained by repeating a following process cycle in a plurality of times. Specifically, a drain current is measured for 120 seconds in a state in which a voltage of 7.5 V is applied to the gate electrode 13*g* and a voltage of 0.5 V is applied to the drain electrode 13*d*, and then, keeping of a state, in which the voltage that is applied to the gate electrode 13*g* and the drain electrode 13*d* is set to 0 V, is performed for 120 seconds. In an operation state in which the voltage of 7.5 V is applied to the gate electrode 13*g* and the voltage of 0.5 V is applied to the drain electrode, the following state is observed. Specifically, an initial drain current value of approximately 220 nA is observed, and a variation, in which the drain current value decreases by several nA after 120 seconds, is observed.

After keeping the gate voltage and the drain voltage to 0 V for 120 seconds, when restarting measurement by setting the gate voltage and the drain voltage to 7.5 V and 0.5 V, respectively, attention is given to a variation in the drain current value. This variation represents that the drain current value is recovered from a drain current value (value decreased from 220 nA by several nA) at the time of termination of the immediately previous measurement to an initial value of approximately 220 nA.

Due to this variation, it is possible to suppress a drift during measurement, or it is possible to periodically initialize a sensor state while denying a variation due to the drift. Furthermore, in the case of assuming that the drift continues even for 120 seconds for which the gate voltage and the drain voltage are kept to 0 V, it is expected that the drain current value becomes a value that further decreases from the value, which decreased from 220 nA by several nA, by several nA immediately before restarting measurement. However, even in this case, when restarting measurement, the decrease in the drain current is canceled, and thus the drain current value is recovered to the initial value of approximately 220 nA.

In the case of assuming that a time constant of drain current attenuation is constant, it is possible to realize measurement with high accuracy in consideration of the above-described drift by reading out a drain current after passage of a constant time from an operation of the TFT biosensor.

In this example, as a voltage condition in the idle period, 0 V is selected for both the gate voltage and the drain voltage. However, there is no limitation thereto, and only the gate voltage may be set to 0 V, or only the drain voltage may be set to 0 V. The voltage value in the idle period may be a value of 0 V or less, and may be a value of 0 V or greater as long as the transistor 39 can be controlled in an OFF-state. In this case, the microprocessor 38 controls the ON/OFF state of the transistor 39 so as to change the drain voltage (voltage between the source electrode 13*s* and the drain electrode 13*d*) with a unit time interval (for example, for every 120 seconds). In addition, when the drain voltage is equal to or greater than a predetermined value (threshold value), the microprocessor 38 applies the output voltage Vout1, which is calculated based on the voltage value (input voltage Vin) acquired from the current-voltage conversion circuit 41, to the gate electrode 13*g*. In this case, in a case where the drain voltage is less than the predetermined value, the microprocessor 38 does not apply a voltage to the gate electrode 13*g*, and thus intermittent measurement based on a value of the drain voltage becomes possible.

In addition, in this example, the description has been given of the result obtained by measurement at a cycle of 120 seconds, but an appropriate measurement period may be selected as long as the drift can be suppressed or canceled. For example, the same effect is obtained with a pulse operation, and an operation can be performed by a sine wave, a rectangular wave, and a triangular wave. In addition, for example, when the pulse operation is performed at a frequency of 100 Hz or greater, an effect of suppressing occurrence of the drift is obtained in a pseudo manner, and measurement with high stability can be realized.

Modulation of the operation voltage, and generation of the pulse can be easily realized by the microprocessor 38 illustrated in FIG. 15.

The circuit configuration and the operation principle, which are described in the eighth embodiment and Examples 11 and 12, are applicable to the first to seventh embodiments and Examples 1 to 10 which correspond thereto. Further, the circuit configuration and the operation principle are also applicable to an ion sensor (sensor that detects a specific ion concentration in a test liquid without using enzyme reaction) in which the enzyme 19 does not exist in the configuration of respective examples.

In addition, the circuit configuration and the operation principle, which are described in the eighth embodiment and Examples 11 and 12, are not limited to the configuration in which the concentration (pH) of hydrogen ions varies due to enzyme reaction, and the concentration of biomaterial is sensed by detecting the pH variation. The circuit configuration and the operation principle are also applicable to a configuration of sensing a concentration of an arbitrary ion that is generated in the enzyme reaction. For example, in the case of performing sensing of a test liquid in which a cation such as Na ion and K ion is generated in the enzyme reaction, a thin film, which is formed by mixing a compound including polypeptide such as valinomycin or crown ether that becomes a ligand as a basic skeleton, and a resin material, and by applying and baking the resultant mixed material, is applicable to the ion-sensitive insulating film 14. Even in the case of an anion without limitation to the cation, it is possible to use a ligand that is appropriate to the anion.

According to the disclosure, it is possible to realize the biosensor capable of detecting with high sensitivity the extremely minute pH variation caused by enzyme reaction.

In addition, the above-described biosensor is applicable to a high-sensitivity biosensor that is used in medical, welfare, and environmental fields. When using the oxide semiconductor TFT as an interfacial potential detection mechanism, it is possible to realize high-sensitivity sensing beyond the sensitivity according to the Nernst theory. In addition, when forming enzyme, which is a biological material recognition mechanism, on an insulating substrate that is different from a substrate on which the TFT is formed, application to bio-sensing is possible without damaging high-sensitivity sensing characteristics. In addition, the configuration in which the enzyme is fixed to the different insulating substrate leads to the configuration in which replacement of the enzyme substrate is possible, and thus it is possible to recover a decrease in a function due to inactivation of enzyme. From these characteristics, the biosensor can be used for a disease marker examination and biomarker examination in a clinical examination.

It is to be noted that the disclosed embodiment is illustrative and not restrictive in all aspects. The scope of the present technique is defined by the appended claims rather than by the description preceding them, and all changes that fall within metes and bounds of the claims, or equivalence of such metes and bounds thereof are therefore intended to be embraced by the claims.

It is to be noted that, as used herein and in the appended claims, the singular forms "a", "an", and "the" include plural referents unless the context clearly dictates otherwise.

What is claimed is:

1. A biosensor, comprising:
a semiconductor active layer;
a gate insulating film that is provided on a first surface of the semiconductor active layer, and insulates the semiconductor active layer and a gate electrode from each other;
an ion-sensitive insulating film that is provided on a second surface of the semiconductor active layer, and includes a region that comes into contact with a solution; and
an enzyme that is fixed at a position spatially separated from the ion-sensitive insulating film, and reacts with a material in the solution to allow a potential variation in the region to occur,
wherein an electrostatic capacity per unit area of the ion-sensitive insulating film is greater than an electrostatic capacity per unit area of the gate insulating film.

2. The biosensor according to claim 1, further comprising:
a detection unit that detects a potential on the ion-sensitive insulating film after amplifying the potential with a value of a ratio obtained by dividing the electrostatic capacity per unit area of the ion-sensitive insulating film by the electrostatic capacity per unit area of the gate insulating film.

3. The biosensor according to claim 1, further comprising:
a mechanism that controls a flow of a sensing object material between the ion-sensitive insulating film and the enzyme that is fixed to the position spatially separated from the ion-sensitive insulating film.

4. The biosensor according to claim 1,
wherein the semiconductor active layer is an oxide semiconductor or an organic semiconductor.

5. A biosensor, comprising:
a semiconductor active layer;
a first gate insulating film that is provided on a first surface of the semiconductor active layer, and insulates the semiconductor active layer and a first gate electrode from each other;
a second gate insulating film that is provided on a second surface of the semiconductor active layer;
a second gate electrode that is provided on the second gate insulating film, and extends to a position that is two-dimensionally spaced away from a region overlapping with the semiconductor active layer;
an ion-sensitive insulating film that is provided on the second gate electrode, and includes a region that comes into contact with a solution; and
an enzyme that is fixed to a position spatially separated from the ion-sensitive insulating film, and reacts with a material in the solution to allow a potential variation in the region of the ion-sensitive insulating film to occur,
wherein an electrostatic capacity per unit area of the second gate insulating film is greater than an electrostatic capacity per unit area of the first gate insulating film.

6. The biosensor according to claim 5, further comprising:
a detection unit that detects a potential on the ion-sensitive insulating film after amplifying the potential with a value of a ratio obtained by dividing the electrostatic capacity per unit area of the second gate insulating film by the electrostatic capacity per unit area of the first gate insulating film.

7. The biosensor according to claim 5, further comprising:
a mechanism that controls a flow of a sensing object material between the ion-sensitive insulating film and the enzyme that is fixed to the position spatially separated from the ion-sensitive insulating film.

8. The biosensor according to claim 5, further comprising:
a first substrate on which the first gate electrode, the first gate insulating film, the semiconductor active layer, the second gate insulating film, the second gate electrode, and the ion-sensitive insulating film are formed; and
a second substrate in which the enzyme is fixed,
wherein the second substrate includes a groove in one surface, and the enzyme is fixed to an inner surface of the groove, and
the first substrate and the second substrate are disposed in a state in which the ion-sensitive insulating film and the enzyme face each other.

9. The biosensor according to claim 5,
wherein the first gate electrode, the first gate insulating film, the semiconductor active layer, the second gate insulating film, the second gate electrode, and the ion-sensitive insulating film are formed on a first substrate in this order, and
the enzyme, which reacts with the material in the solution to allow the potential variation in the region of the ion-sensitive insulating film to occur, is fixed onto a second substrate.

* * * * *